US012588900B2

(12) United States Patent
Donovan et al.

(10) Patent No.: US 12,588,900 B2
(45) Date of Patent: **\*Mar. 31, 2026**

(54) SALIVA ASSESSING METHOD, DEVICE, AND SYSTEM

(71) Applicant: Boka Sciences, Inc., Sandy, UT (US)

(72) Inventors: Grant J. Donovan, Salt Lake City, UT (US); Jeffrey A. Stern, Beverly Hills, CA (US); Ryan C. Patterson, Farmington, UT (US); James A. Malmstrom, Kaysville, UT (US); Kent F. Beck, Layton, UT (US); Scott D. Miles, Sandy, UT (US)

(73) Assignee: BOKA SCIENCES, INC., Sandy, UT (US)

( * ) Notice: Subject to any disclaimer, the term of this patent is extended or adjusted under 35 U.S.C. 154(b) by 10 days.

This patent is subject to a terminal disclaimer.

(21) Appl. No.: 18/620,909

(22) Filed: Mar. 28, 2024

(65) Prior Publication Data

US 2024/0237974 A1     Jul. 18, 2024

Related U.S. Application Data

(60) Continuation of application No. 16/940,360, filed on Jul. 27, 2020, now Pat. No. 11,944,279, which is a (Continued)

(51) Int. Cl.
*A61B 10/00*          (2006.01)
*A61B 5/00*          (2006.01)
(Continued)

(52) U.S. Cl.
CPC ........ *A61B 10/0051* (2013.01); *A61B 5/4277* (2013.01); *A61B 5/682* (2013.01);
(Continued)

(58) Field of Classification Search
None
See application file for complete search history.

(56) References Cited

U.S. PATENT DOCUMENTS

| | | | | |
|---|---|---|---|---|
| 4,112,066 A | * | 9/1978 | Hussein | A61K 8/365 |
| | | | | 424/48 |
| 4,689,214 A | * | 8/1987 | Niles | A61Q 11/00 |
| | | | | 514/901 |

(Continued)

FOREIGN PATENT DOCUMENTS

WO      WO 2014/028687      2/2014

OTHER PUBLICATIONS

International Search Report dated Feb. 23, 2018 for International Application No. PCT/US2017/066443 (10 Pages).

(Continued)

*Primary Examiner* — Michael R Bloch
(74) *Attorney, Agent, or Firm* — David L. Stott

(57) ABSTRACT

Various embodiments of a swab device, system, and method are provided for measuring and assessing saliva flow in the mouth of a person. In one embodiment, a system includes a swab device and a measuring device. The swab device includes a handle portion and a swab portion, the handle portion being elongated to extend between a proximal end and a distal end. The swab portion is coupled to a distal portion of the handle portion and is sized and configured to collect saliva from the mouth. The measuring device is sized and configured to measure an amount of the saliva collected with the swab portion, the measuring device including a nesting portion integrated therewith. Such nesting portion of the measuring device is sized and configured to receive the proximal end of the handle portion of the swab device to measure the saliva collected therewith.

12 Claims, 11 Drawing Sheets

Related U.S. Application Data division of application No. 15/839,844, filed on Dec. 12, 2017, now Pat. No. 10,736,612.

(60) Provisional application No. 62/434,386, filed on Dec. 14, 2016.

(51) Int. Cl.
    *A61J 1/10*           (2006.01)
    *A61B 5/145*          (2006.01)

(52) U.S. Cl.
    CPC .............. *A61J 1/10* (2013.01); *A61B 5/0077* (2013.01); *A61B 5/14539* (2013.01); *A61B 5/746* (2013.01)

(56) References Cited

U.S. PATENT DOCUMENTS

| | | | |
|---|---|---|---|
| 6,152,887 | A | 11/2000 | Blume |
| 6,623,698 | B2 | 9/2003 | Kuo |
| 7,883,724 | B2 | 2/2011 | Konrad |
| 8,287,809 | B2 | 10/2012 | Gould et al. |
| 9,113,850 | B2 | 8/2015 | Skakoon |
| 2001/0008614 | A1 | 7/2001 | Aronowitz |
| 2002/0155029 | A1* | 10/2002 | Mink ................. A61B 10/0051 |
| | | | 436/162 |
| 2006/0073538 | A1 | 4/2006 | Konrad |
| 2009/0024060 | A1 | 1/2009 | Darrigrand et al. |
| 2010/0174156 | A1 | 7/2010 | Patel et al. |
| 2012/0310113 | A1 | 12/2012 | Giddings et al. |
| 2013/0072851 | A1* | 3/2013 | Doll ..................... A61C 17/221 |
| | | | 604/20 |
| 2014/0187890 | A1* | 7/2014 | Mensinger ........... A61B 5/0004 |
| | | | 600/365 |
| 2015/0216471 | A1* | 8/2015 | Goldstein .............. A61B 5/682 |
| | | | 600/573 |
| 2016/0135728 | A1 | 5/2016 | Furukawa et al. |
| 2017/0124264 | A1* | 5/2017 | Jordan ................... G16H 10/40 |

OTHER PUBLICATIONS

"Saliva Parameters as Potential Indices of Hydration Status during Acute Dehydration," Niel P. Walsh, Stewart J. Laing, Samuel J. Oliver, Joanna C. Montague, Robert Walters, James L. J. Bilzon, Medicine & Science In Sports & Exercise, pp. 1535-1542, Sep. 2004.

"Is This Elderly Patient Dehydrated? Diagnostic Accuracy of Hydration Assessment Using Physical Signs, Urine, and Saliva Markers," Matthew B. Fortes, Julian A. Owen, Philippa Raymond-Barker, Claire Bishop, Salah Elghenzai, Samuel J. Oliver, Neil p. Walsh, Journal Of The American Medical Directors Association, pp. 1-8, Oct. 2014.

"Diagnosis And Management Of Xerostomia And Hyposalivation," Alessandro Villa, Christopher L. Connell, Silvio Abati, Therapeutics and Clinical Risk Management, Dovepress, Dec. 22, 2014.

"Saliva Collectors, Chapter 4 by Arjan Vissink, Andy Wolff, Enno C.I. Veerman," Salivary Diagnostics, Wiley-Blackwell, Mar. 2008.

"Xerostomia and Salivary Gland Hypofunction by A.M.L Pedersent, p. 8," Dry Mouth: A Clinical Guide on Causes, Effects and Treatments, 2015.

"Dry Mouth—An Overview by Ngo Di Ying Joanna, William Murray Thomson," Singapore Dental Journal 36, Elsevier (2015).

"A quantitative test for xerostomia. The saxon test, an oral equivalent of the schirmer test by Peter F. Kohler MD, Margaret E. Winter," Arthritis & Rheumatism / vol. 28, Issue 10, Abstract, Oct. 1985, located at http://onlinelibrary.wiley.com/doi/10.1002/art.1780281008/full.

"Effectiveness of Electrostimulation on Whole Salivary Flow Among Patients with Type 2 Diabetes Mellitus by Sujatha Dyasnoor, Shwetha Kamath, Nishat Fatima Abdul Khader," The Permanente Journal, Apr. 21, 2017, published online at https://www.ncbi.nlm.nih.gov/pmc/articles/PMC5424585/.

"Salivary Flow Estimation—An Alternate and Non-Invasive Method by Naveen Srinivas, Ketki Sali, Praveen Kumar Ramurg, Anju Anu Jose, Sneha C. Khanapure," Indian Journal of Medical Research and Pharmaceutical Sciences, Aug. 2017, published online at http://ijmrps.com/Issues%20PDF/Vol.4/August-2017/4.pdf.

Wikipedia, Xerostomia, Sep. 19, 2018, published online at https://en.wikipedia.org/wiki/Xerostomia#Diagnostic_approach.

"Test for Saliva Secretion Rate" Published by University of Malmo (2018) located online at https://www.mah.se/fakulteter-och-omraden/Odontologiska-fakulteten/Avdelning-och-kansli/Cariologi/Cariology/Caries-risk-assessment/Diagnostics---Dental-Care/Test-for-Saliva-Secretion-Rate/.

Measurement of Whole Unstimulated Salivary Flow in the Diagnosis of Sjogren's Syndrome by Paul M. Speight, Arvind Kaul, Richard D. Melsom, Annals of the Rheumatic Diseases (1992) located online at https://www.ncbi.nlm.nih.gov/pmc/articles/PMC1004700/?page=2.

Protocol from Johns Hopkins Sjogrens Center titled Sialometry, located online at https://www.hopkinssjogrens.org/disease-information/diagnosis-sjogrens-syndrome/sialometry/.

"Measuring Salivary Flow by Mahvash Navazesh, Satish K.S. Kumar," JADA, vol. 139 (May 2008), published online at http://jada.ada.org/article/S0002-8177(14)63880-0/pdf.

"A Systematic Review of Methods to Diagnose Oral Dryness and Salivary Gland Function by Christina Diogo Lofgren, Claes Wickstrom, Mikael Sonesson, Pablo Tapia Lagunas, Cecilia Christensson," BioMed Central, Aug. 8, 2012, published online at https://www.ncbi.nlm.nih.gov/pmc/articles/PMC3573918/.

\* cited by examiner

82

90

90

86

84

80

82

80

84

88

82

SALIVA ASSESSING METHOD, DEVICE, AND SYSTEM

CROSS-REFERENCE TO RELATED APPLICATIONS

The present application is a continuation of U.S. patent application Ser. No. 16/940,360, filed on Jul. 27, 2020, which is a divisional of U.S. patent application Ser. No. 15/839,844, filed Dec. 12, 2017, now U.S. Pat. No. 10,736, 612, which claims the benefit of U.S. Provisional Application No. 62/434,386, filed Dec. 14, 2016, the disclosures of which are hereby incorporated by reference herein in their entirety.

TECHNICAL FIELD

The present invention relates generally to xerostomia or reduced saliva flow and, more specifically, the present invention relates to devices, systems and methods for assessing saliva flow.

BACKGROUND

Dry mouth, also known as xerostomia, is the medical term for the subjective complaint of having a dry mouth or lack of saliva. Dry mouth can lead to problems of tooth decay, the ability to swallow, and the ability to taste and digest food, among other things. Physicians and dentists continue to seek diagnostic devices and methods for determining or assessing the condition of xerostomia or dry mouth by measuring a saliva flow rate produced by the glands in the mouth. The apparent most widely used method for determining saliva flow rate within a patient is by conducting a drool test. For example, the drool test is implemented with a drool cup, in which a patient leans over the cup with his or her head tilted forward and the mouth open to allow drool produced by the saliva glands to flow over the bottom lip and into the drool cup. Such test is typically timed over a five or ten minute time period. At the end of the time period, a saliva flow rate may be determined by the amount of saliva collected into the drool cup relative to the time period taken to collect the saliva. This known method for determining saliva flow rate for a given person has often been found to be inaccurate due to the difficulty in conducting the test and the close supervision and patient compliance required. Further, the drool test is inefficient since the typical time frame just to collect the saliva sample is five to ten minutes. Furthermore, from a patient's standpoint, drooling into a cup is degrading, humiliating, cumbersome and uncomfortable, especially when conducted with staff, doctors and/or family members present.

Based on the foregoing, it would be advantageous to provide a device, system and/or method that substantially overcomes the above-noted limitations for determining a patient's saliva flow rate and related data.

BRIEF SUMMARY OF THE INVENTION

The present invention is directed to various embodiments of devices, systems and methods for assessing saliva flow from saliva glands in a mouth of a person, such as a patient. In one embodiment, a saliva assessment system for measuring saliva flow in a mouth of a person is provided. The saliva assessment system includes a swab device and a measuring device. The swab device includes a handle portion and a swab portion, the handle portion being elongated to extend between a proximal end and a distal end. The swab portion is coupled to a distal portion of the handle portion and is sized and configured to collect saliva from the mouth. The measuring device is sized and configured to measure an amount of the saliva collected with the swab portion, the measuring device including a nesting portion integrated therewith. The nesting portion is sized and configured to receive the handle portion of the swab device.

In another embodiment, the swab device includes a base structure at the proximal end of the handle portion, the base structure sized and configured to nest with the nesting portion of the measuring device such that the swab device is positionable with the nesting portion in an erect manner. In another embodiment, the handle portion extends with a first surface and a second surface along a longitudinal length of the handle portion, the first surface facing opposite relative to the second surface. The distal portion of the handle portion includes a first protrusion and a second protrusion positioned to extend from the first surface and the second surface, respectively, the first and second protrusions configured to facilitate coupling the swab portion to the handle portion.

In still another embodiment, the swab portion extends with an elongated flat structure having a first end portion and a second end portion, the elongated structure folded over the distal end of the handle portion so to cover opposite sides of the distal portion of the handle portion. In a further embodiment, the swab portion defines a first slit and a second slit in the first end portion and the second end portion, respectively, the first slit sized and configured to couple to a first protrusion extending from the handle portion and the second slit sized and configured to couple to a second protrusion extending from the handle portion.

In another embodiment, the handle portion of the swab device extends with one or more curves along a length of the handle portion. In yet another embodiment, the swab portion includes at least one of a foam material, a fabric material, and a natural fiber material, the swab portion configured to absorb the saliva from the mouth. In another embodiment, the measuring device includes a scale portion integrated adjacent the nesting portion of the measuring device, the scale portion configured to measure a weight of the saliva captured by the swab portion.

In another embodiment, the measuring device includes an integrated computing device, the integrated computing device being operatively coupled to at least one of a remote database and a local computing device, each of the at least one of the remote database and the local computing device being configured to receive and store patient data received from the integrated computing device and process the patient data, the at least one of the remote database and the local computing device configured to send processed patient data to the integrated computing device of the measuring device. In a further embodiment, the processed patient data includes a patient data index number.

In another embodiment, the system further includes a local computing device for entering patient data obtained from the measuring device, the local computing device being operatively coupled to a remote database, the remote database configured to receive and store the patient data and process the patient data, the remote database configured to send the processed patient data to the local computing device. In a further embodiment, the processed patient data includes a patient data index number. In another embodiment, the measuring device is operatively coupled to a local computing device, the local computing device configured to transmit to and receive data from at least one of a remote database and the measuring device.

In accordance with another embodiment of the present invention, a swab device configured to measure saliva flow in a mouth of a person is provided. The swab device includes a handle portion and a swab portion. The handle portion extends between a proximal end and a distal end to define an elongated structure along a length thereof. The handle portion includes a flat base structure at the proximal end of the handle portion, the flat base structure extending trans- verse relative to the elongated structure of the handle portion. The swab portion is coupled to a distal portion of the handle portion, the swab portion being sized and configured to collect saliva from the mouth.

In another embodiment, the handle portion defines a width and a depth, the depth being smaller than the width of the handle portion, the width extending with a first surface and an oppositely facing second surface along the length of the handle portion. In another embodiment, the handle portion extends with a first surface and a second surface along the length of the handle portion, the first surface facing oppositely relative to the second surface. The distal portion of the handle portion includes a first protrusion and a second protrusion positioned to extend from the first surface and the second surface, respectively, such that the swab portion is coupled to the first and second protrusions.

In another embodiment, the swab portion extends with a flat elongated sheet structure having a first end portion and a second end portion, the elongated structure folded over the distal end of the handle portion so that the first and second end portions couple to opposite sides of the distal portion of the handle portion. In still another embodiment, the swab portion defines a first slit and a second slit in the first end portion and the second end portion, respectively, of the flat elongated sheet structure, the first and second slits config- ured to couple to the opposite sides of the distal portion of the handle portion.

In another embodiment, the handle portion of the swab device extends with one or more curves along a length of the handle portion. In yet another embodiment, the handle portion includes a tapered portion along a length of the handle portion.

In still another embodiment, the swab portion includes at least one of a foam material, a fabric material, and a natural fiber material. In another embodiment, the swab portion is a flat sheet structure folded over the distal end of the handle portion so that the flat sheet structure exhibits a bowed portion.

In accordance with another embodiment of the present invention, a method for measuring saliva flow in a mouth of a person is provided. The method includes the steps of: clearing excess saliva from the mouth; inserting a swab into the mouth for a first predetermined period of time ranging between about 1 second and about 20 seconds; and measur- ing an amount of saliva captured by the swab by positioning the swab on a measuring device.

In another embodiment, the method further includes com- paring the measured amount of saliva with a standard healthy saliva amount to determine whether to continue testing the saliva flow of the person. In still another embodi- ment, the method further includes determining whether the measured amount of saliva is below a standard healthy saliva amount. In another embodiment, the method further includes: maintaining the mouth in a closed position for a second predetermined period of time ranging between about 3 second and about 90 seconds; inserting a second swab into the mouth for a third predetermined period of time ranging between about 1 second and about 20 seconds; and measur- ing an amount of saliva captured by the second swab by positioning the second swab on the measuring device.

In accordance with another embodiment of the present invention, a method for measuring saliva flow in a mouth of a person is provided. The method includes the steps of: clearing excess saliva from the mouth; maintaining the mouth in a closed position for a first predetermined period of time ranging between about 3 seconds and about 90 seconds; inserting a swab into the mouth for a second predetermined period of time ranging between about 1 second and about 20 seconds; and measuring an amount of saliva captured by the swab by positioning the swab on a measuring device.

In another embodiment, subsequent to the step of clear- ing, the method includes the steps of: inserting a pre-test swab into the mouth for a pre-test predetermined period of time ranging between about 1 second and about 20 seconds; measuring an amount of saliva captured by the pre-test swab by positioning the pre-test swab on the measuring device; and determining whether the measured amount of saliva by the pre-test swab is below a standard saliva amount to warrant proceeding with the maintaining step.

In another embodiment, the inserting step includes insert- ing the swab for the second predetermined period of time that ranges between about 1 second and about 10 seconds. In another embodiment, the inserting step includes inserting the swab for the second predetermined period of time that ranges between about 1 second and about 5 seconds. In another embodiment, the inserting step comprises inserting the swab for the second predetermined period of time that ranges between about 1 second and 3 seconds. In still another embodiment, the inserting step includes inserting the swab for the second predetermined period of time of about 3 seconds. In yet another embodiment, the maintain- ing step includes maintaining the mouth in the closed position for about 60 seconds for the first predetermined period of time.

In another embodiment, the clearing step includes clear- ing the excess saliva by inserting a secondary swab in the mouth for a period of time ranging between about 1 second and 5 seconds. In still another embodiment, the clearing step includes clearing the excess saliva by inserting a portion of a secondary swab in the mouth for a period of time of about 3 seconds.

In another embodiment, the measuring step includes positioning a proximal end of a handle of the swab in an aperture defined in structure disposed above the measuring device. In another embodiment, the measuring step includes weighing the swab to determine a weight of the saliva.

In still another embodiment, the inserting step includes inserting the swab having a handle portion and a swab portion such that the swab portion includes a hydrophilic foam configured to absorb fluid. In another embodiment, the inserting step includes inserting the swab having a handle portion and a swab portion such that the swab portion includes a reticulated foam material configured to absorb fluid. In yet another embodiment, the inserting step includes inserting the swab having a handle portion and a swab portion, the swab portion extending in a flat configuration with a distal peripheral edge and a proximal peripheral edge, the distal peripheral edge extending substantially linearly and the proximal peripheral edge extending radially.

In accordance with another embodiment of the present invention, a saliva assessment system for measuring saliva flow in a mouth of a person is provided. The saliva assess- ment system includes a swab device and a measuring device.

The swab device is sized and configured to be placed in the mouth such that the swab device includes a handle portion and a swab portion. The handle portion extends between a proximal end and a distal end, the distal end coupled to the swab portion. The swab portion extends with a flat configuration to define a peripheral edge. The peripheral edge extending along a distal peripheral edge and a proximal peripheral edge, the distal peripheral edge extending linearly and the proximal peripheral edge extending radially. The measuring device is sized and configured to measure an amount of the saliva collected in the swab portion from the mouth. Further, the measuring device includes a nesting portion coupled thereto. The nesting portion defines an aperture therein, the aperture sized and configured to receive a proximal end of the handle portion of the swab device.

In another embodiment, the swab portion exhibits a half oval configuration sized and configured to be positioned under a tongue in the mouth. In another embodiment, the measuring device includes a scale portion configured to measure a weight of the saliva captured by the swab portion. In another embodiment, the handle portion extends with a curve along a distal portion of the handle portion.

In another embodiment, the swab portion includes a hydrophilic material configured to absorb fluid. In another embodiment, the swab portion includes a polymeric material configured to absorb fluid. In still another embodiment, the swab portion includes a reticulated material configured to absorb fluid. In yet another embodiment, the swab portion includes a foam material configured to absorb fluid. In another embodiment, the swab portion includes a fabric material configured to absorb fluid. In another embodiment, the swab portion includes a reticulated, hydrophilic polyurethane foam material configured to absorb fluid.

In another embodiment, the measuring device includes an integrated computing device, the integrated computing device being operatively coupled to a remote database configured to receive and store patient data received from the integrated computing device and process the patient data. Such remote database is configured to send processed patient data to the integrated computing device of the measuring device. In another embodiment, the processed patient data may include a patient data index number.

In another embodiment, the system further includes a local computing device for entering patient data, the local computing device being operatively coupled to a remote database. Such remote database is configured to receive and store the patient data and process the patient data such that the remote database is configured to send the processed patient data to the local computing device. In another embodiment, the processed patient data includes a patient data index number.

In accordance with another embodiment of the present invention, a swab device configured to measure saliva flow in a mouth of a person is provided. The swab device includes a handle portion and a swab portion. The handle portion extends between a proximal end and a distal end thereof. The swab portion is coupled to the distal end of the handle portion. The swab portion extends in a flat configuration to define a peripheral edge, the peripheral edge extending to define a distal peripheral edge and a proximal peripheral edge. The distal peripheral edge extends substantially linearly and is configured to be positioned under a tongue in the mouth and adjacent a rear side thereof. The proximal peripheral edge extends radially and is configured to be positioned under the tongue and adjacent an inner surface of bottom teeth in the mouth.

In another embodiment, the swab portion includes a hydrophilic material configured to absorb liquid. In another embodiment, the swab portion includes a polymeric material configured to absorb liquid. In still another embodiment, the swab portion includes a reticulated material configured to absorb liquid. In yet another embodiment, the swab portion includes a foam material configured to absorb liquid. In another embodiment, the swab portion includes a fabric material configured to absorb liquid. In another embodiment, the swab portion includes a hydrophilic polyurethane foam material configured to absorb liquid. In still another embodiment, the handle portion extends with a curve along a distal portion of the handle portion.

In accordance with another embodiment of the present invention, a swab device configured to measure saliva flow in a mouth of a person is provided. The swab device includes a case and a swab portion. The case includes a clam shell arrangement with a first case portion and a second case portion. The first case portion is pivotably coupled to the second case portion such that the case is moveable between an open position and a closed position. The swab portion is coupled to an inner surface of at least one of the first case portion and the second case portion of the case. Upon the case being in the closed position, the swab portion is sized and configured to be enclosed in the case. Further, upon the case being moved to the open position, at least one of the first case portion and the second case portion are sized and configured to facilitate handling the swab portion to position the swab portion within the mouth.

In another embodiment, upon the case being in the closed position, the first case portion substantially seals with the second case portion. In another embodiment, the first case portion and the second case portion are maintainable in the closed position with a snap type fit. In another embodiment, the swab portion includes a handle coupled to the case. In still another embodiment, the swab portion is moveable to be oriented at an angle relative to the inner surface of one of the first and second case portions of the case. In another embodiment, the first case portion is pivotably coupled to the second case portion with at least one of a hinge and a living hinge.

In another embodiment, the swab portion includes a hydrophilic material configured to absorb fluid. In another embodiment, the swab portion includes a polymeric material configured to absorb fluid. In still another embodiment, the swab portion includes a reticulated material configured to absorb fluid. In yet another embodiment, the swab portion includes a foam material configured to absorb fluid. In another embodiment, the swab portion includes a fabric material configured to absorb fluid. In another embodiment, the swab portion includes a reticulated, hydrophilic polyurethane foam material configured to absorb fluid.

In accordance with another embodiment of the present invention, a saliva assessment system for measuring saliva flow in a mouth of a person is provided. The saliva assessment system includes a swab device and a measuring device. The swab device is sized and configured to be placed in the mouth, the swab device having a handle portion and a swab portion. The handle portion extends between a proximal end and a distal end, the distal end coupled to the swab portion. The measuring device is sized and configured to measure an amount of the saliva collected on the swab portion from the mouth.

In one embodiment, the swab portion includes an upper portion and a lower portion with a proximal extension therebetween, the swab portion defining a gap between the upper portion and the lower portion on a distal side of the swab portion such that the gap is sized and configured to receive a tongue of the person. In another embodiment, the swab portion includes a distal side, the distal side defining an opening therein, the opening sized and configured to receive a tongue of the person. In another embodiment, the swab portion includes a top surface and a bottom surface each defining a curved channel therein, the curved channel sized and configured to receive respective upper and lower teeth of the person. In still another embodiment, the swab portion includes an upper surface, a bottom surface, and a distal surface. The upper and bottom surfaces define curved channels therein sized and configured to receive teeth of the patient. The distal surface defines an opening therein sized and configured to receive a tongue of the person. In yet another embodiment, the swab portion includes an elongated curved structure. In still another embodiment, the swab device includes a straight handle.

In another embodiment, the swab portion includes a natural fiber configured to absorb liquid. In another embodiment, the swab portion includes a polymeric material configured to absorb liquid. In still another embodiment, the swab portion includes at least one of a foam material, a fabric material, and a natural fiber material. In another embodiment, the measuring device is a digital scale. In still another embodiment, the measuring device is a vibration measuring device. In still another embodiment, the measuring device is an optical measuring device.

BRIEF DESCRIPTION OF THE SEVERAL VIEWS OF THE DRAWINGS

The foregoing and other advantages of the invention will become apparent upon reading the following detailed description and upon reference to the drawings in which.

DETAILED DESCRIPTION OF THE INVENTION

Figure 1:
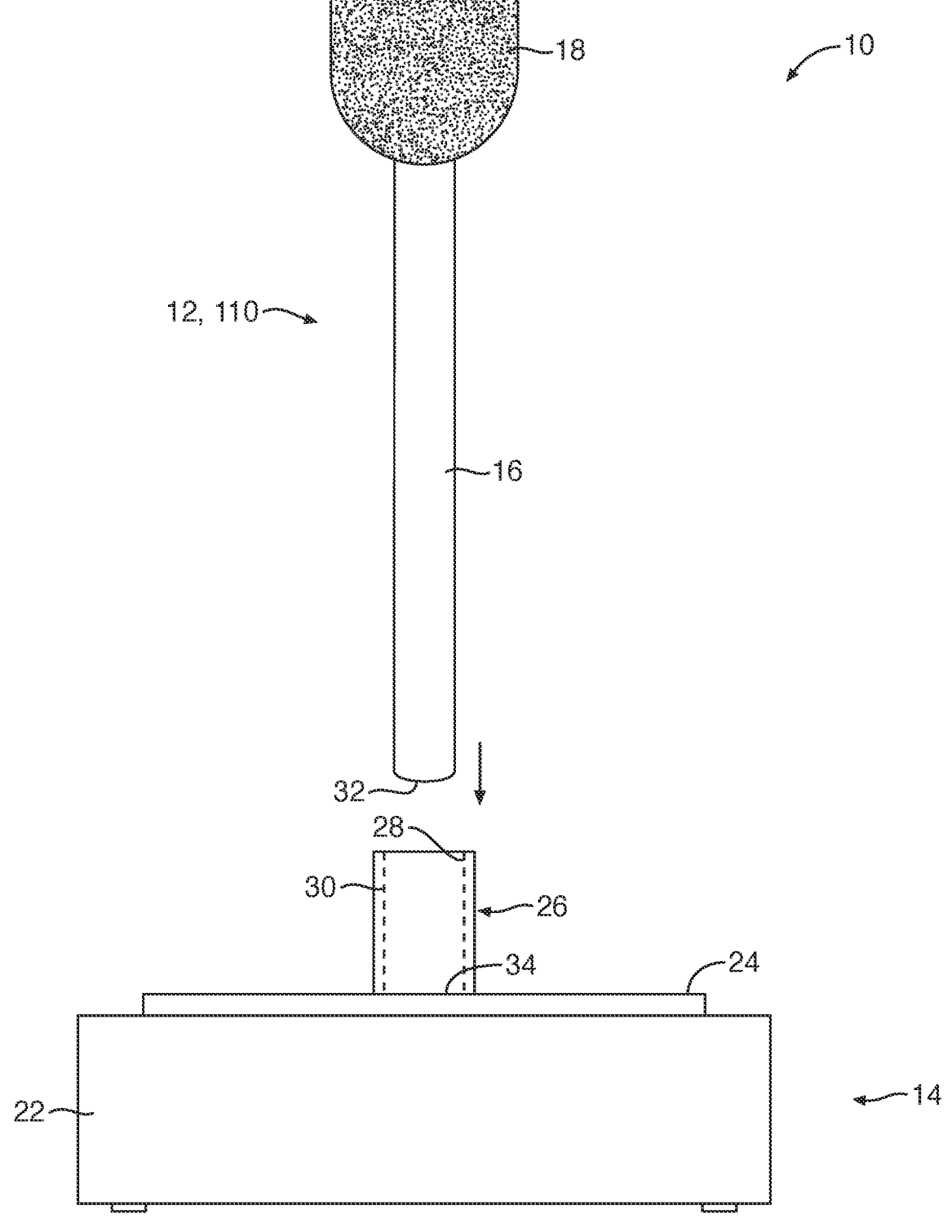
FIG. 1 is a front view of a saliva assessment system, depicting a swab device and a measuring device, according to one embodiment of the present invention.

Referring to FIG. 1, one embodiment of a saliva assessment system 10 is provided. The saliva assessment system 10 may be employed to measure saliva flow rate of a patient. The method for determining saliva flow rate in a patient set forth herein may be relatively quick and may be conducted in a manner that is more likely to be tolerated by the patient as well as maintaining the dignity and removing the uncomfortable or embarrassing factor from the patient. In one embodiment, the saliva assessment system 10 may include a swab device 12 and a measuring device 14, the swab device 12 having a handle portion 16 and a swab portion 18. The saliva assessment system 10 may also include a method and system for storing data, such as a local and/or a remote database 20 (FIG. 7) that may be configured to receive and send data, discussed in further detail herein.

The saliva assessment system 10 may be employed for the purpose of determining whether the patient has the condition known as xerostomia or dry mouth. The saliva assessment system 10 may be configured to measure saliva flow rate in the mouth of the patient. Saliva flow rate may be defined as and determined by measuring a volume of fluid for a particular time period. Further, the volume of the saliva may be determined from, for example, a measured weight or other unit of measurement of the saliva collected from the patient.

For example, to obtain a saliva sample, the patient may clear any excess saliva from the mouth and, then, the patient may maintain the mouth in a closed position for a first predetermined time period without swallowing. The patient may then take the swab device 12 by the handle portion 16 and insert the swab portion 18 into the mouth for a second predetermined period of time, the swab portion 18 being a material configured to collect saliva so as to absorb or draw and wick the saliva therewith and maintain such saliva within the swab portion 18. The swab device 12 may then be placed on the measuring device 14 to, for example, obtain a weight of the saliva absorbed within the swab portion 18 of the swab device 12. With such saliva weight obtained relative to the first predetermined period of time, the saliva flow rate of the patient may be determined and assessed relative to all known factors of the patient. In this manner, multiple samples may be taken from the patient at one sitting or at different times of the day and/or on different days to obtain data points for a particular patient and determine and assess a condition of such patient. With this arrangement, the saliva assessment system 10 may be employed to determine whether a patient has a "dry mouth" condition so that the patient can undergo steps and procedures for increasing mouth hydration and averting the serious consequences of not treating the dry mouth condition.

In one embodiment, the measuring device 14 may be a digital scale sized and configured to measure weight to a relatively high degree of accuracy, such as to 0.001 grams of accuracy or greater. The digital scale may function similar to digital scales known in the art, the digital scale having a base 22 and a scale portion 24. The scale portion 24 may be positioned along an upper side of the base 22 and the scale portion 24 may be sized to receive an object or substance thereon to be weighed. The digital scale may perform common functions of most digital scales, such as a "Tare" function, as known to one of ordinary skill in the art. The "Tare" function allows one to "zero-out" the weight of an item placed on the scale portion 24, such as a container, to then place an additional item in the container and on the scale to determine the weight of the additional item.

The measuring device 14 of the present invention may include a nesting portion 26. In one embodiment, the nesting portion 26 may include structure for receiving the handle portion 16 of the swab device 12. Such nesting portion 26 may be configured to receive the swab device 12, such as the handle portion 16, in a manner that prevents contamination of an obtained saliva sample such that the swab portion 18 may not be touched through the process of weighing the obtained saliva sample. The nesting portion 26 may include various structures to receive the handle portion 16 of the swab device 12. For example, as depicted, the nesting portion 26 may be in the form of a cylindrical structure 30 or tubular structure with an aperture 28 or opening defined therein. The aperture 28 may be sized with a dimension larger than the handle portion 16 to facilitate ready positioning of the handle portion 16 therein. In one embodiment, the aperture 28 may be sized so that the handle portion 16 may loosely fit into the aperture in a non-constricted arrangement, such that a proximal end 32 of the swab device 12 simply rests at a bottom end 34 of the nesting portion 26 or directly against a top surface of the scale portion 24. In this manner, such aperture 28 defined in the nesting portion 26 of the measuring device 14 may be sized to receive the handle portion 16 to facilitate weighing an obtained saliva sample without a user or patient contacting the swab portion 18 after obtaining the saliva sample, thereby, preventing the potential of contaminating or altering the saliva sample.

In another embodiment, the nesting portion may be a platform positioned above the scale portion. The platform may include an aperture defined therein. Similar to the previous embodiment, the aperture may be sized larger than width and thickness dimensions of the handle portion. In one embodiment, the aperture may be in the form of a slot. As can be appreciated, other structures of the nesting portion may also be employed so long as the nesting portion is sized to receive the handle portion 16 of the swab device 12. For example, in one embodiment, the nesting portion may be in the form of a recess defined in the scale portion (see e.g., FIGS. 18-19).

The measuring device 14 may measure a weight or volume of saliva collected in a swab portion 18 of the swab device 12 employing various devices other than the before-discussed digital scale. For example, in another embodiment, the measuring device 14 may be in the form of a natural frequency or vibrational type device such that, upon collecting a saliva sample with the swab portion, the handle may be positioned in a nesting portion of the vibrational device. The natural frequency of the swab device with the collected saliva sample can be determined and compared with the natural frequency of the swab device without the collected saliva sample. The weight or volume of the saliva can then be determined with the measuring device 14 in the form of a vibrational device. In another embodiment, the measuring device 14 may be an optical measuring device. In this embodiment, the optical measuring device may measure saliva within the swab portion by measuring light transmission through the swab portion without the collected saliva sample in comparison with the collected saliva sample. In this manner, weight or volume of the saliva sample may be determined with an optical measuring device. As set forth, the measuring device 12 employed with the saliva assessment system 10 may measure different aspects of the swab device with the collected saliva sample in order to determine the amount of saliva collected in the swab portion.

Figure 2:
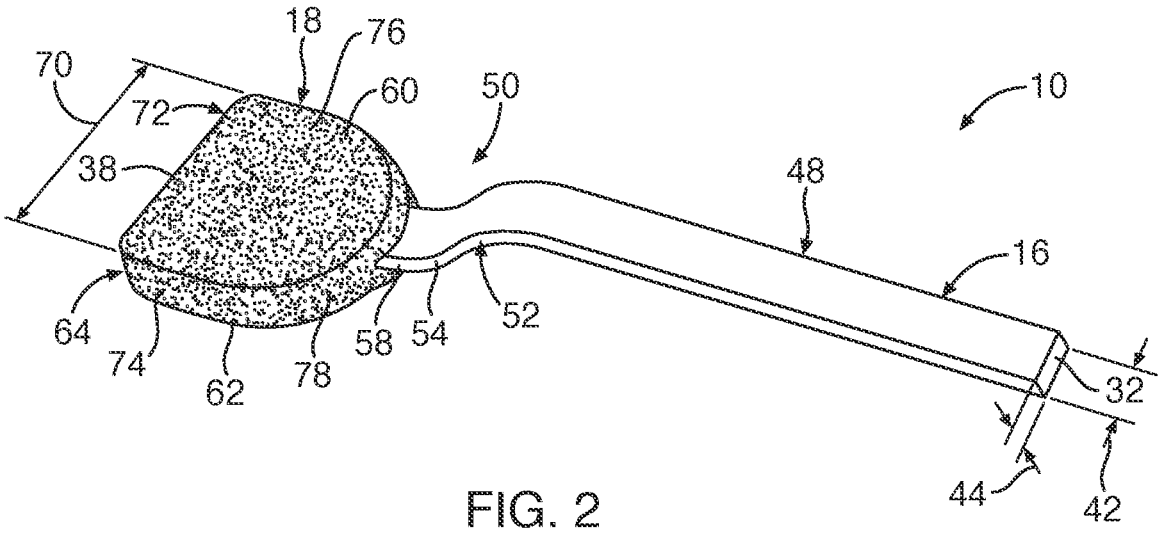
FIG. 2 is a perspective view of the swab device, according to another embodiment of the present invention.
Figure 3:
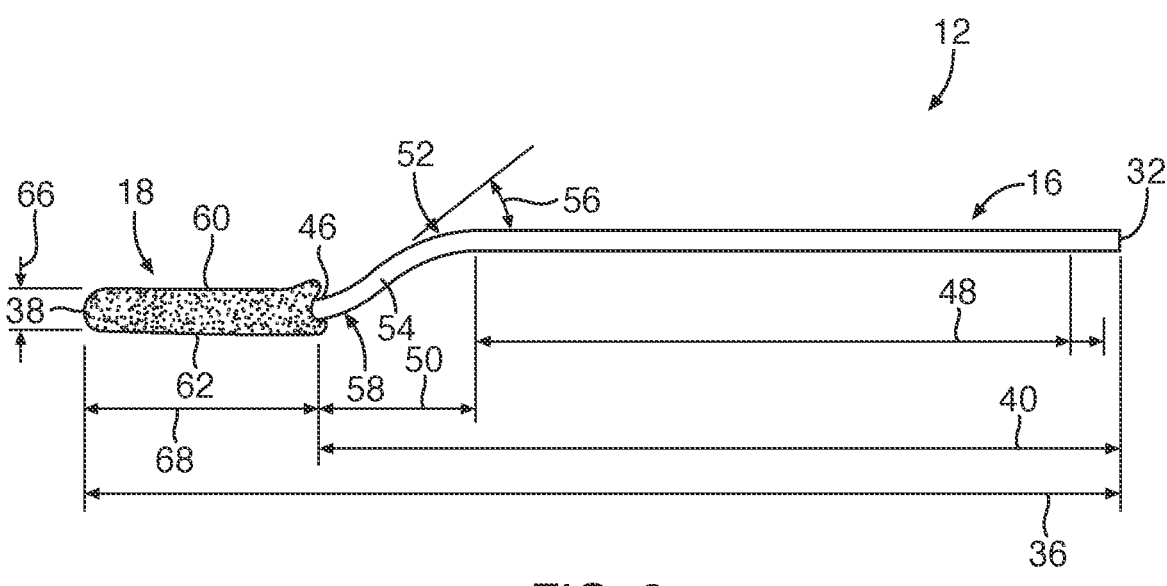
FIG. 3 is a side view of the swab device, according to another embodiment of the present invention.

Now with reference to FIGS. 2 and 3, detail relative to the swab device 12 will now be described. As previously set forth, the swab device 12 may include the handle portion 16 and the swab portion 18. The swab device 12 may be elongated to define a longitudinal length 36 extending between the proximal end 32 and a distal end 38 of the swab device 12.

The handle portion 16 may be sized and configured to be readily grasped and held by a patient or user. The handle portion 16 may include an elongated structure extending with a handle length 40, a handle width 42, and a handle thickness 44. The handle portion 16 may extend longitudinally along the handle length 40 between the proximal end 32 of the swab device 12 and a handle distal end (not shown), the distal end being positioned within the swab portion 18. In other words, the handle distal end and a distal end portion 46 may be disposed within the swab portion 18 for coupling thereto. Further, along the handle length 40, the handle portion 16 may define the proximal end 32, a mid portion 48, and a distal handle portion 50. The mid portion 48 may extend distal the proximal end 32 to the distal handle portion 50. The mid portion 48 may be the portion of the handle portion 16 employed primarily for grasping the swab device 12. The handle length 40 may extend anywhere between one to nine inches or more, for example. The handle width 42 may extend, for example, anywhere between about 0.125 to 0.75 inches with a handle thickness 44 about 0.125 inches. It should be noted that the invention is not limited to such handle dimensions. The handle width 42 may be a constant width or may vary along the handle length such that the mid portion 48 may be wider than that of the distal handle portion 50, for example.

In one embodiment, the distal handle portion 50 of the handle portion 16 may extend from the mid portion 48 with a curve 52. For example, from the mid portion 48 of the handle portion 16 toward the distal end, the distal handle portion 50 may extend with a downward extending portion 54 such that the downward extending portion 54 may define an angle 56 relative to the mid portion 48 of the handle portion 16. The downward extending portion 54 may extend with the curve 52 or radius from the mid portion 48 to the distal end portion 46 of the handle portion 16. The downward extending portion 54 may extend to a second curve 58 or radius adjacent to the swab portion 18. Distal the second curve 58, the swab portion 18 may be coupled to the remaining portion of the handle portion 16 at its distal end portion 46. With this curve or downward extending portion 54, as a user positions the swab portion 18 in the mouth, such as under the tongue, such curve or downward extending portion 54 facilitates the handle portion 16 to extend at a preferred orientation that allows the user to readily position the swab portion 18 under the tongue in the mouth while holding the handle portion 16.

In one embodiment, the handle portion 16 may be formed from a suitable polymeric material, such as polypropylene or polystyrene, or any other suitable polymeric material. Further, such handle portion 16 may be formed by employing any suitable molding techniques, as known to one of ordinary skill in the art. In another embodiment, the handle portion 16 may be formed by employing die cutting techniques, heat forming techniques or extruding techniques, as known to one of ordinary skill in the art. In another embodiment, the handle portion 16 may be formed of a metallic material or a suitable wood material.

As previously set forth, the swab portion 18 may be coupled to the distal end or the distal end portion 46 of the handle portion 16. The swab portion 18 may be sized and configured to be positioned within a mouth of a patient, such as under the tongue within the mouth. In one embodiment, the swab portion 18 may be a substantially flat configuration. The swab portion 18 may include a top surface 60 and a bottom surface 62 with a peripheral edge 64 therebetween that defines a swab thickness 66 of the swab portion 18. The swab portion 18 may extend with a swab length 68, a swab width 70, and the swab thickness 66, the swab length 68 corresponding with the longitudinal length of the handle portion 16 and the swab width 70 extending laterally relative to the longitudinal length of the handle portion 16.

In one embodiment, the top surface 60 and the bottom surface 62 of the swab portion 18 may be shaped similarly so as to exhibit a half oval configuration. The peripheral edge 64 of the swab portion 18 may define a distal peripheral edge 72, a first side peripheral edge 74, a second side peripheral edge 76, and a proximal peripheral edge 78. From a top view, the distal peripheral edge 72 of the swab portion 18 may extend linearly and correspond with the lateral width dimension. The surface of the distal peripheral edge 72 may extend flat or may include a curvature, as depicted in FIG. 3, extending between the top surface 60 and the bottom surface 62 of the swab portion 18. The first and second side peripheral edges 74, 76 may each extend linearly from the distal peripheral edge 72, at for example a right angle, and then begin to extend radially inward at the proximal peripheral edge 78 such that the proximal peripheral edge 78 is curved and extends radially. With this arrangement, the swab portion 18 may be sized to be positioned under a user's tongue such that the swab portion 18 may be positioned in the space between the teeth and the tongue. For example, the distal peripheral edge 72 may be positioned rearward under the tongue, the first and second peripheral edges 74, 76 may be positioned under the tongue and adjacent opposite first and second inner sides of the bottom teeth and a curved portion of the proximal peripheral edge 78 can be disposed adjacent and along an inner side of the front bottom teeth.

In one embodiment, the swab portion 18 may be formed from a polymeric material configured to absorb liquid. In another embodiment, the swab portion 18 may be formed from a foam material. In another embodiment, the swab portion 18 may be formed from open-cell or reticulated foam, a reticulated polymeric material, and/or a hydrophilic foam material. In another embodiment, the swab portion 18 may be formed from medical grade polymeric foam, such as, polyurethane foam, silicon foam, polyvinyl alcohol (PVA) foam, or any other suitable polymeric foam configured to absorb liquid. In another embodiment, the swab portion 18 may be formed from a fabric or felt of natural and/or polymeric fibers sized and configured to absorb liquid. In another embodiment, the swab portion 18 may be formed from cotton fibers.

In another embodiment, the swab portion 18 may be formed by cutting or stamping the swab portion 18 from sheet material. For example, the swab portion 18 may be cut to correspond with the size/shape of the swab portion 18, as depicted in FIG. 2, with a central cut-out sized for receiving the distal end portion 46 of the handle portion 16. Such coupling may be employed with adhesive or a heat staking process, as known to one of ordinary skill in the art. In one embodiment, the thickness 66 of the swab portion 18 may be about 0.25 inches, or in the range of about 0.125 and 0.5 inches. In another embodiment, the thickness 66 of the swab portion may be in the range of about 0.5 inches to about 1.5 inches with similar swab length 68 and swab width 70 dimensions sized to be positioned under a patient's tongue. In another embodiment, the swab portion 18 may be formed with any suitable molding technique.

Figures 4, 5, 6:
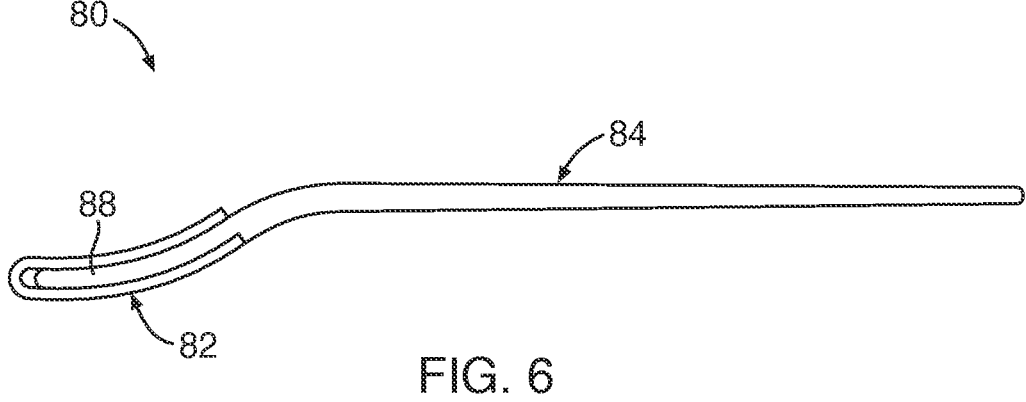
FIG. 4 is a top view of a swab portion, depicting the swab portion in a pre-formed state, according to another embodiment of the present invention.
FIG. 5 is a perspective view of another embodiment of a swab device, according to the present invention.
FIG. 6 is a side view of the swab device of FIG. 5, according to another embodiment of the present invention.

Now with reference to FIGS. 4-6, another embodiment of a swab device 80 is depicted. In this embodiment, the swab portion 82 and handle portion 84 may be sized and configured to function in a similar manner as the previous embodiment, depicted and described relative to FIG. 2, except the swab portion 82 may be cut from sheet material in the form of an oval shape, for example. In this embodiment, the thickness of the sheet material may be about 0.125 inches or greater. As depicted in FIG. 4, the oval shaped sheet material may be folded over at its mid portion, as depicted by first dotted line 86, to form the swab portion 82 in the half oval configuration. Similar to the previous embodiment, the folded over sheet material may result in thickness of the swab portion being about 0.25 inches or greater, such as a range between 0.25 inches to about 1.5 inches, depending upon the desired thickness of swab portion 82. As in the previous embodiment, the handle portion 84 may be coupled to the swab portion 82 at a distal end portion 88 of the handle portion 84. For example, the distal end portion 88 of the handle portion 84 may be positioned between the two folded-over ends, contacting the material, as depicted at second dotted lines 90 (depicting a profile of the distal end portion 88 of the handle portion 84), for coupling the material of the swab portion 82 to the distal end portion 88 of the handle portion 84. Such coupling may be employed with adhesive and/or a heat staking process or any other suitable coupling process, such as a mechanical type hook or latch coupling, known in the art. For example, a heat staking process may be utilized by heating at points or regions to couple both sides of the swab material together and coupling the swab material to the handle portion 84 to, thereby, form the swab device 80.

Figure 7:
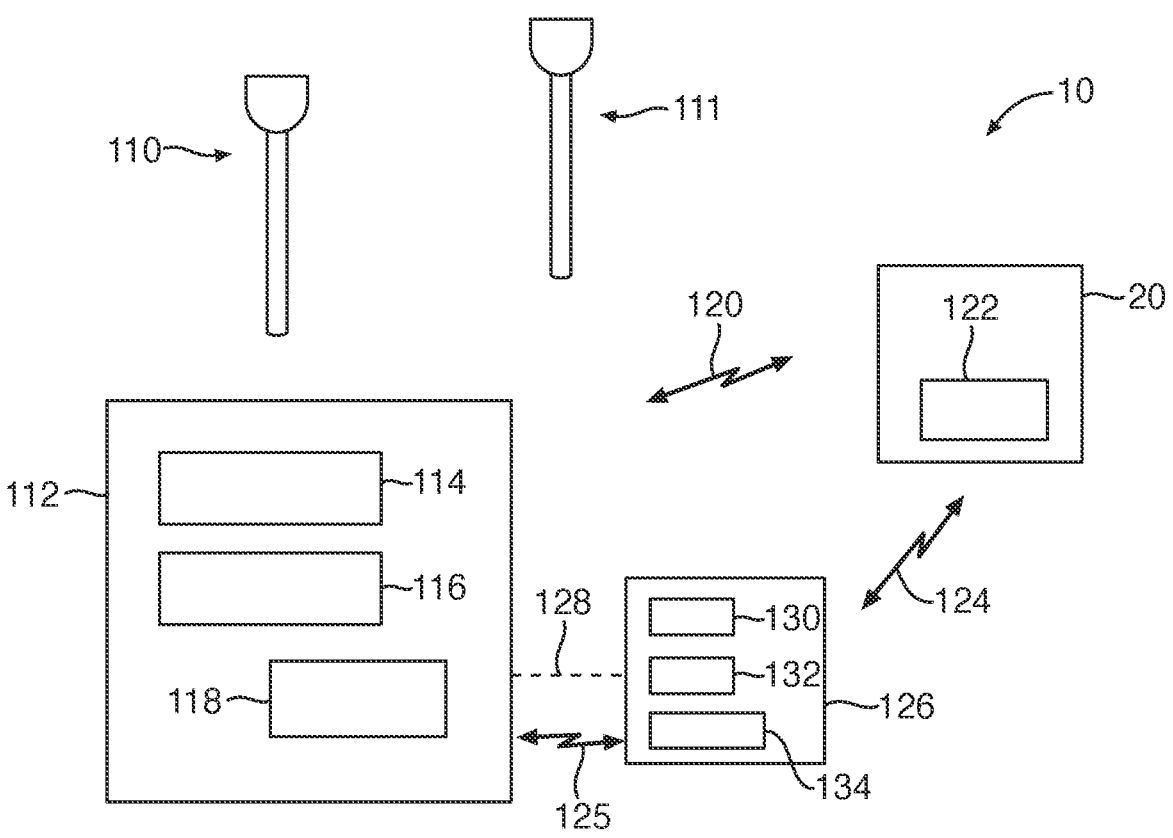
FIG. 7 is a schematic view of a saliva assessment system, according to another embodiment of the present invention.

With respect to FIG. 7, another embodiment of a saliva assessment system 100, depicted in schematic form, is provided. In this embodiment, the saliva assessment system 100 may include a swab device 110 and a measuring device 112, similar to that depicted in FIG. 1. Further, the swab device 110 may be any one of the embodiments set forth herein as a swab device. The measuring device 112 may include an input portion 114 and an output portion 116. The input portion 114 being in the form of input keys, touch screen, switch or the like. The output portion 116 may be in the form of a display to provide, for example, measured or weighed data, or any other relevant data. In one embodiment, the measuring device 112 may also include a computing device 118 integrated therein sized and configured to send and receive data, as indicated by communication arrow 120 so as to communicate with a remote system, such as the before discussed remote database 20, as known to one of ordinary skill in the art.

Further, in this embodiment, the swab assessment system 100 may include the remote database 20. The remote database 20 may be sized and configured to store data. Further, the remote database 20 may include a remote computing device 122 sized and configured to receive and send data, as indicated by communication arrows 120 and/or 124. In another embodiment, the saliva assessment system 100 may be employed with a local computing device 126, which may be integrated with the measuring device 112 (as indicated by dotted line 128) or be separate of the measuring device 112 so as to be utilized with the measuring device 112 for the user to record detail from the patient along with the measurements taken from the saliva assessment. The local computing device 126 may be a mobile device, such as a mobile phone, tablet or lap-top computer, or may be a stationary computer. As such, the local computing device 126 includes an input device 130 and output device 132. The local computing device 126 may be configured, as known in the art, to send and receive data to and from the remote database, as indicated by communication arrow 124, as well as transmit to send and receive data to and from the measuring device 112, as indicated by communication arrow 125. Such transmissions 125 between the measuring device 112 and the local computing device 126 or the remote database 20 may be employed wirelessly or by, for example, a cable or the like, or may be transferred, for example, with a thumb drive.

Further, for example, upon assessing saliva flow, data about the patient may be input into the local computing device 126, such as an identification number, data regarding the age of the patient, the time/date, the time elapsed since the patient last slept, the time elapsed since the patient last had food and/or water, and/or any other data that may be relevant. Further, the data relating to the measured amount of saliva obtained from the patient may be inputted into the local computing device 126. Such data may then be transmitted or uploaded (or transferred via, for example, a thumb drive) to the remote database as indicated by communication arrow 124. In another embodiment, the data about the patient may be maintained in the measuring device 112 and/or the local computing device 126.

The remote computing device 122 may then process the data received from the local computing device 126 and store the processed data therein, and then transmit the processed data to the local computing device 126 for the doctor to assess and provide to the patient. The processed data may provide the actual saliva flow rate and/or a patient saliva index number that may correspond with or be compared to a scale that may indicate a degree or level of a saliva flow of a patient to determine the degree or severity in which the patient may have the condition of dry mouth or xerostomia. Such patient saliva index number may also be associated with a unique patient identifier. In this manner, the saliva assessment system 100 may include the remote database 20 for storing and processing data and for transmitting the processed data back to the doctor to provide detail about the severity of the condition of the patient. As the remote database 20 continues to grow over time with patients assessed, detail regarding the data taken from the assessed patients relative to the saliva obtained may be helpful in refining the processed data and understanding what factors may be relevant relative to time of day, age, time elapsed since sleep and food eaten, male, female, medications taken/taking, health conditions, etc., to better understand saliva flow rate for a given patient. Further, as the database grows with patient data, the accumulation of multiple patients' data may generate secondary data to provide information that constitutes a standard or normalized healthy saliva flow or a normalized healthy saliva flow relative to various factors relative to, for example, cercadic fluctuations of saliva flow at certain times of day. In this manner, upon obtaining a person's actual saliva flow, the patient's data may be processed relative to the above-noted various factors and algorithmically adjusted or extrapolated to provide an adjusted saliva flow amount. Further, in this manner, upon evaluating a person's actual or adjusted saliva flow, such measurements may be evaluated relative to the accumulation of other patient's data to better understand where that evaluated person's saliva flow is in comparison to other saliva flow data and/or a normalized healthy saliva flow.

In another embodiment, as indicated herein, the measuring device 112 may also be integrated with its own computing device 118. As such, the measuring device 112 may be sized and configured to receive the before-discussed patient data via the input portion 114 to then transmit the data, along with the data relating to the saliva assessment, to the remote database 20. The remote database 20 may then store the received data and process the data to then transmit such processed data to the local computing device 126 and/or the measuring device 112 for the doctor.

In another embodiment, the local computing device 126 may include a local database 134. The local database 134 may perform the same or similar functions as that described for the remote database 20. Further, the local database 134 may work in conjunction with the remote database 20 such that the local database 134 may store and process data and send such data and processed data to also be stored in the remote database 20 as well as be stored in the local database 134. In another embodiment, the local computing device 126 may function with the processing capabilities independent of the remote database such that the local computing device 126 may process data and store the processed data in the local database 134.

Further detail relative to a method for determining saliva flow rate of a patient will now be described. For example, two swab devices may be opened from their respective packaging, a primary swab device, such as swab device 110 and a secondary swab device 111 or pre-test swab device. The measuring device 112 may be activated by powering or turning on the measuring device 112. The user may then place the primary swab device 110 on the scale portion 24 by, for example, placing the proximal end 32 of the handle portion 16 of the swab device 110 in the nesting portion 26 (see FIG. 1). The user may then zero-out the measuring device 112 with the swab device 110 and nesting portion 26 positioned thereon by pressing, for example, the Tare button. In another embodiment, the Tare may be automatic, such as in the case that the weight of the swab device is known. At this juncture, the patient may clear any excess saliva from the mouth. Such may be accomplished by using the tongue to gather any existing saliva in the mouth and discarding the saliva by, for example, swallowing or spitting the saliva. In another embodiment, the process of clearing the excess saliva from one's mouth may include employing, for example, a suction device.

In another embodiment, the process of clearing excess saliva from one's mouth may also include inserting the secondary swab device 111 (the swab device not positioned on the measuring device) into the mouth to further absorb any additional excess saliva. In one embodiment, the secondary swab device 111 may be placed under the tongue and, upon closing the mouth, pressing down on the swab portion with the tongue for a period of time, such as one second or more. In another embodiment, the secondary swab device 111 may be placed under the tongue for a time period ranging between about one second and three seconds, or ranging between about one second and five seconds, or ranging between about one second and ten seconds. In another embodiment, the secondary swab device 111 may be placed under the tongue for about three seconds. In still another embodiment, the secondary swab device 111 may be placed under the tongue for a time period ranging between about one second and about twenty seconds. In this manner, the excess saliva may be cleared or removed from one's mouth. The secondary swab device 111 may then be discarded.

At the instant the secondary swab device 111 is removed from the patient's mouth, the patient may maintain their mouth in a closed position for a first predetermined period of time, such as 60 seconds. In another embodiment, the first predetermined period of time may be in the range of about 15-90 seconds, or about two minutes or about three minutes or any suitable period of time, such as five minutes, so long as the first predetermined period of time is provided as data relative to the saliva sample obtained from the patient. In a preferred embodiment, the first predetermined period of time may be about 60 seconds. As the patient maintains his or her mouth closed during the first predetermined period of time, the patient may tilt his or her head forward slightly with the tongue pressed against the roof of the mouth so that new saliva produced from the saliva glands in the mouth may pool below the patient's tongue. During the first predetermined period of time, the patient may grasp the primary swab device 110 positioned on the measuring device so that immediately after the first predetermined period has lapsed, the patient can place the swab portion of the primary swab device 110 under the tongue in the mouth to collect the accumulated saliva by pressing down onto the swab with the tongue for a second predetermined period of time, such as about three seconds. In one embodiment, the second predetermined period of time may range between about 1 second and about 3 seconds. In another embodiment, the second predetermined period of time may range between about 1 second and about 5 seconds. In still another embodiment, the second predetermined period of time may range between about 1 second and about 10 seconds. Immediately after the second predetermined period of time, the primary swab device 110 with the absorbed saliva may be positioned on the measuring device 112 by, for example, inserting the proximal end 32 of the swab device into the nesting portion 26 of the measuring device 112 (see FIG. 1). The measuring device 112 may then display, for example, the weight of the saliva collected in the swab portion of the primary swab device 110. This displayed weight value may then be recorded and the swab device 110 discarded.

The data received from the patient may then be processed to obtain processed data to compare and determine a degree or level of the condition of the patient relative to dry mouth or xerostomia, as previously described. Further, as previously set forth, in one embodiment, such patient data may be transmitted to the remote database 20 to be processed and to obtain the processed data for the patient. The above-noted procedure may be completed a second time or multiple consecutive times within a given hour or day to take additional samples for the purpose of obtaining average flow rate detail or the like, or to obtain additional information of saliva flow rate relative to different times of the day to better understand a given person's saliva flow rate relative to, for example, potential cercadic fluctuations of the person.

In another embodiment, the secondary swab device 111 or pre-test swab device may be employed prior to using the primary swab device 110 to perform pre-testing to determine if further testing should be completed by the person being tested. Such pre-testing may include the steps of clearing saliva from the mouth, such as by spitting or swallowing the excess saliva from one's mouth. Upon clearing the mouth of excess saliva, then the person may insert a swab device, such as the pre-test swab device or secondary swab device 111 for a predetermined period of time or pre-test predetermined period of time. This pre-test predetermined period of time may range between about 1 second and about 20 seconds, or about 1 second and about 10 seconds, or any suitable period of time. In one embodiment, the pre-test swab may be placed under the person's tongue. Subsequent the pre-test period of time, the person may remove the pre-test swab and then measure the amount of saliva captured by the pre-test swab by positioning the pre-test swab device on the measuring device 112. Upon determining the amount of saliva captured by the pre-test swab for the pre-test predetermined period of time, such saliva amount may be compared with a standard healthy saliva amount. In one embodiment, if the saliva amount obtained from the person is greater than the standard healthy saliva amount, then the person may stop in being further tested. If the saliva amount obtained is less than the standard healthy saliva amount, then the person may undergo further testing. For example, the person may then undergo the testing procedure of clearing excess saliva from the mouth, maintaining the mouth in a closed position for a predetermined period of time, such as ranging between about 3 seconds and about 90 seconds, inserting the primary swab 110 into the mouth for another predetermined period of time, such as ranging between about 1 second and about 20 seconds, and then measuring the amount of saliva captured by the primary swab 110 by positioning the primary swab on the measuring device 112 to obtain, for example, a weight of the saliva captured by the primary swab 110. As previously set forth, the various patient data and results of the testing may then be recorded to the remote database 20 and/or the local computing device 126.

Figure 8:
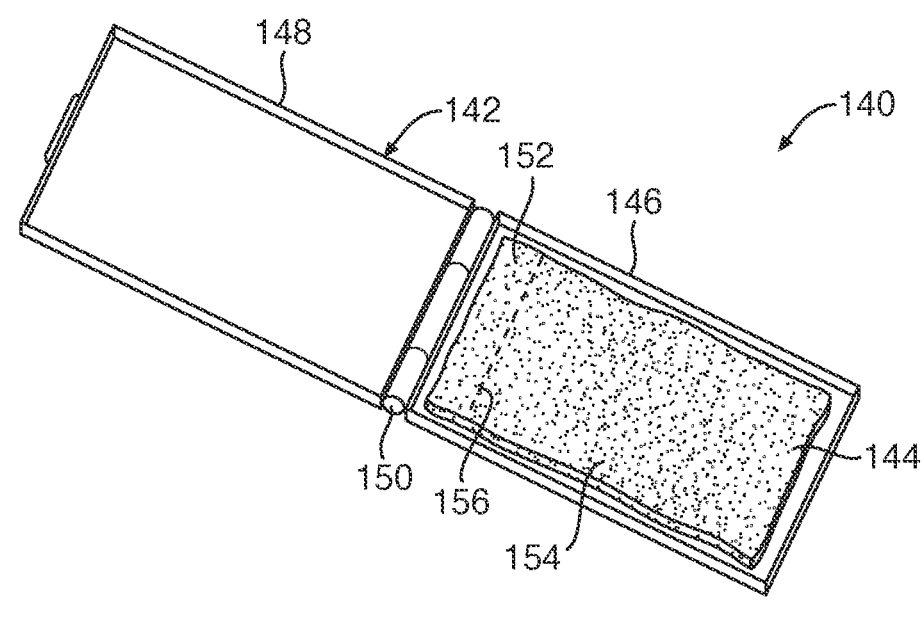
FIG. 8 is a perspective view of another embodiment of a swab device, depicting the swab device having a case in an open position with a swab portion coupled to the case, according to the present invention.
Figure 9:
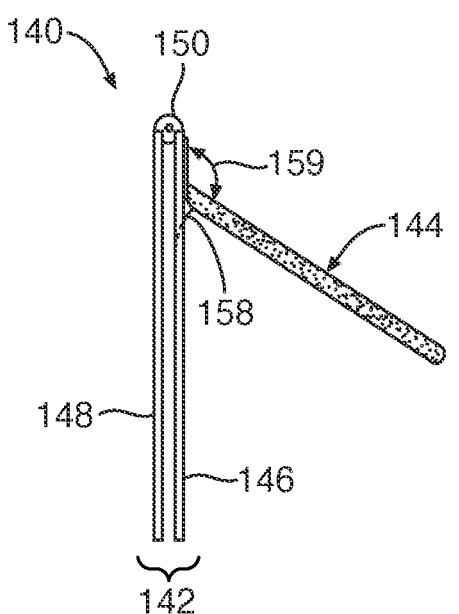
FIG. 9 is a side view of the swab device of FIG. 8, depicting the case in an open position or use position with the swab portion biased outward, according to another embodiment of the present invention.
Figure 10:
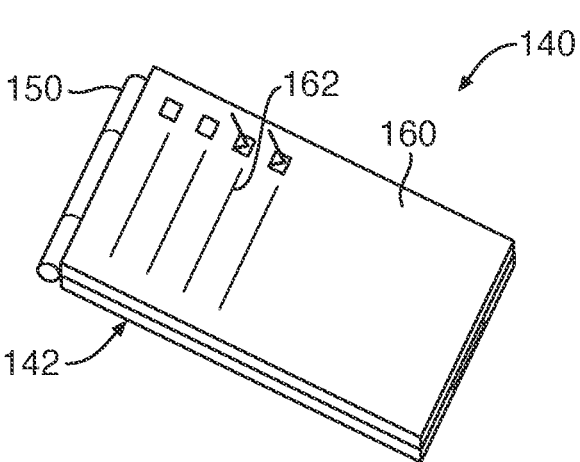
FIG. 10 is a perspective view of the swab device of FIG. 8, depicting the case in a closed position, according to another embodiment of the present invention.

Now with reference to FIGS. 8-10, another embodiment of a swab device 140 is depicted. The swab device 140 of this embodiment may be employed, for example, when taking saliva samples from a large number of patients. For example, the swab device 140 of this embodiment may include a case 142 or container and a swab portion 144, the swab portion 144 being coupled to the case 142 and enclosable within the case 142. The case 142 may be formed from a polymeric material, as known to one of ordinary skill in the art. The case 142 may include a first case portion 146 that may be pivotably coupled to a second case portion 148 in a clam shell arrangement. In one embodiment, the first and second case portions 146, 148 may be coupled with a hinge 150. In another embodiment, the first and second case portions 146, 148 may be coupled with a living type hinge. With this arrangement, the case 142 may be moved between a closed position (FIG. 10) and an open positon (FIGS. 8 and 9). Further, as set forth, the first and second case portions 146, 148 may be sized to hold the swab portion 144 therein. As such, the shape and size dimensions of the first and second case portions 146, 148 may correspond with the sizing of the swab portion 144 and, in another embodiment, any additional components that may be coupled to the swab portion, such as a handle component.

In one embodiment, the swab portion 144 may exhibit a flat configuration with a rectangular periphery. The swab portion 144 may include a first portion 152 and a second portion 154 defined by dotted lines 156. The first portion 152 of the swab portion 144 may be adhesively coupled to an inner surface of the first case portion 146. The second portion 154 of the swab portion 144 may be freely lifted or moveable relative to the first case portion 146, as depicted in FIG. 9. In another embodiment, upon opening the case 142, the swab portion 144 may be biased to extend outward at an angle 159 relative to the first case portion with, for example a biasing element 158 or the like.

In another embodiment, in the open position, one of the first case portion 146 or the second case portion 148, or both, may act as a handle portion for the swab device 140. With this arrangement, a patient may open the case 142, as depicted in FIG. 9, to position the swab portion 144 in his or her mouth for the before-discussed second predetermined period of time to absorb the accumulated saliva (after undergoing the procedure of accumulating saliva in the mouth for a first predetermined period of time, as discussed above). Immediately after the second predetermined period of time, the swab portion 144 may be removed from the mouth and the case 142 moved to the closed position, as depicted in FIG. 10.

In one embodiment, the case 142 may be maintained in its closed position with a snap type lock. In another embodiment, in the closed position, the case 142 may be configured to be substantially sealed with the swab portion 144 therein. In still another embodiment, the outer surface 160 of the case 142 may be marked with data detail of the patient, for example, a patient identification number and any other relevant patient data, as indicated by indicia 162. At a later time, the swab device 140 with the case 142 may be weighed to determine the saliva amount or saliva flow rate or the like, similar to that discussed in previous embodiments. With this arrangement, the swab device 140 with the case 142 facilitates administering a saliva flow rate assessment to a large volume of patients or in circumstances where the measuring device 112 (FIG. 7) may not be readily available in the patient's room.

Figure 11:
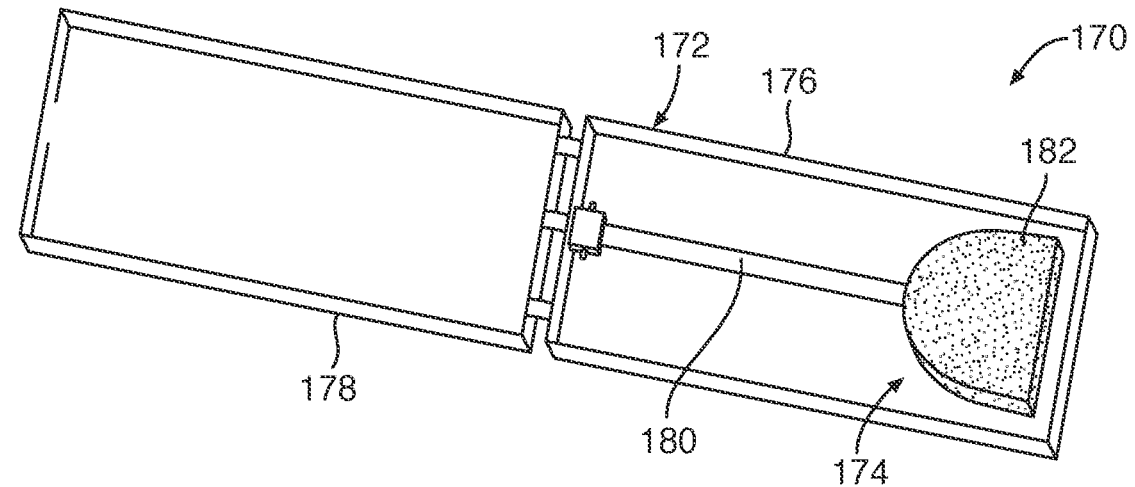
FIG. 11 is a perspective view of another embodiment of a swab device, depicting the swab device having a case in an open position with a swab portion coupled to the case, according to the present invention.

With reference to FIG. 11, another embodiment of a swab device 170 is provided. In this embodiment, the swab device

170 may include a case 172 and a swab portion 174 similar to the previous embodiment such that the case 172 is moveable between an open position, as depicted in FIG. 11, and a closed position, similar to FIG. 10 of the previous embodiment. As such, the case 172 may include a first case portion 176 and a second case portion 178. In this embodiment, the swab portion 174 may include an intermediate member or handle 180 with a swab 182 at a distal end of the handle 180. The handle 180 may be coupled to a portion of the case 172, such as the first case portion 176, at a proximal end of the handle 180. In another embodiment, the handle 180 may be coupled to or adjacent the hinge between the first and second case portions 176, 178. The swab 182 may include a similar shape as the swab portion described and depicted relative to FIG. 2, or any of the embodiments set forth herein. Further, in this embodiment, upon the case 172 being moved to an open position, the handle 180 may be moveable to an orientation or an angle that extends outward relative to the first case portion 176, similar to that depicted in FIG. 9. In this manner, a patient may readily grasp the handle and/or at least one of the first and second portions 176, 178 and position the swab in his or her mouth to collect a saliva sample, employing a similar procedure for collecting the saliva sample described in previous embodiments. The case 172 may then be moved to the closed position for later weighing of the saliva sample.

Figure 12:
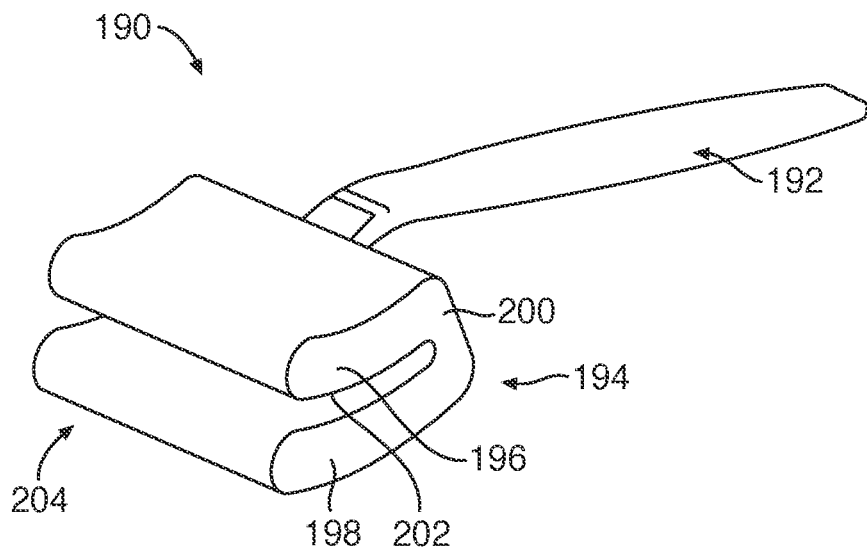
FIG. 12 is a perspective view of another embodiment of a swab device, depicting a swab portion with a gap at a distal side of the swab device, according to the present invention.

Now with reference to FIGS. 12-16, various embodiments of a swab device that may be employed with the saliva assessment system 100 (FIG. 7) are provided. For example, FIG. 12 is another embodiment of a swab device 190 that may include a handle portion 192 and a swab portion 194, the handle portion 192 being similar to previous embodiments as depicted in FIGS. 2 and 5. In this embodiment, the swab portion 194 may include an upper portion 196 and a lower portion 198 with a proximal extension 200 coupling the upper and lower portions 196, 198. The upper and lower portions 196, 198 may define an opening 202 therebetween such that the opening is on a distal side 204 of the swab portion 194. Such opening 202 may be in the form of a gap or channel or the like and may be sized and configured to receive the tongue of the patient. In this manner, the lower portion 198 may absorb saliva that may collect under the tongue and the upper portion 196 may absorb saliva above the tongue and adjacent the cheek regions.

Figure 13:
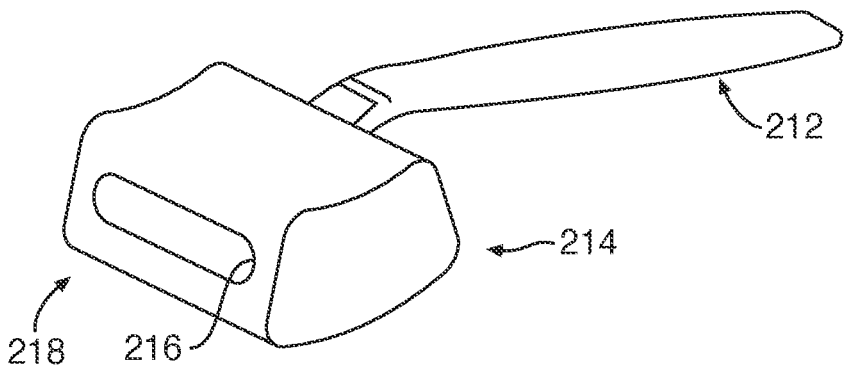
FIG. 13 is a perspective view of another embodiment of a swab device, depicting a swab portion with an opening at a distal side of the swab device, according to the present invention.

With respect to FIG. 13, another embodiment of a swab device 210 that may include a handle portion 212 and a swab portion 214 is depicted. This embodiment is similar to the previous embodiment such that the swab portion 214 defines an opening 216 on a distal side 218 of the swab portion 214 that may be sized and configured to receive the tongue of the patient. The swab portion 214 may be somewhat block-like but may define any other suitable shape.

Figure 14:
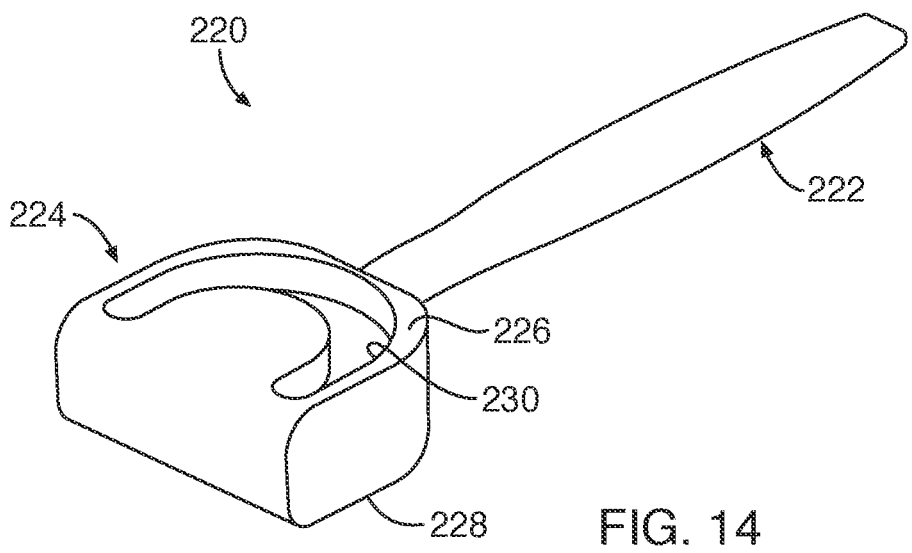
FIG. 14 is a perspective view of another embodiment of a swab device, depicting a swab portion with channels defined therein, according to the present invention.

With reference to FIG. 14, another embodiment of a swab device 220 that may include a handle portion 222 and a swab portion 224. The handle portion 222 in this embodiment may be similar to the previous embodiments as depicted in FIGS. 2 and 5. In another embodiment, the handle portion 222 may be straight (without the bend or curve along the distal handle portion). Further, in this embodiment, the swab portion 224 may be sized and configured to receive at least a portion of the teeth of the patient. As such, the swab portion may define a top surface 226 and a bottom surface 228 each defining a curved channel 230 therein, the curved channel sized and configured to receive the patient's teeth.

Figure 15:
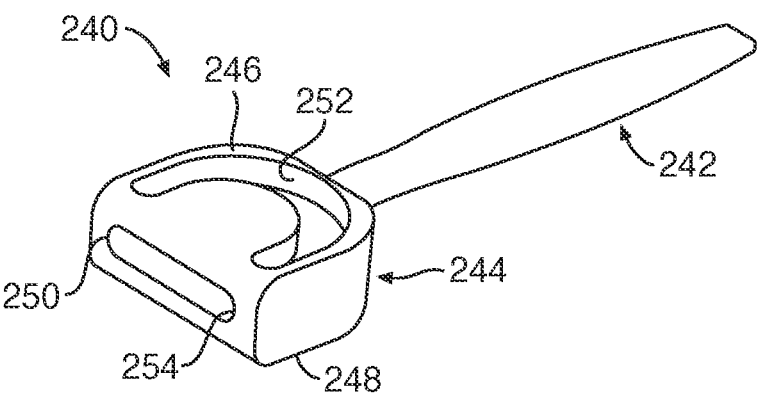
FIG. 15 is a perspective view of another embodiment of a swab device, depicting a swab portion defining an opening and channels therein, according to the present invention.

With respect to FIG. 15, another embodiment of a swab device 240 with a handle portion 242 and a swab portion 244 is provided. This embodiment may include structural features similar to the embodiments of FIGS. 13 and 14. The swab device 240 of this embodiment may include a top surface 246, a bottom surface 248, and a distal surface 250, each of which may define structure for receiving the teeth and tongue of the patient. For example, the top surface 246 and the bottom surface 248 of the swab portion 244 may each define a curved channel 252 therein for receiving respective upper and lower teeth of the patient. Further, the distal surface 250 of the swab portion 244 may define an opening 254 therein sized and configured to receive the tongue of the patient. In this manner, the swab device 240 of this embodiment may be configured to collect saliva at multiple locations within the patient's mouth.

Figure 16:
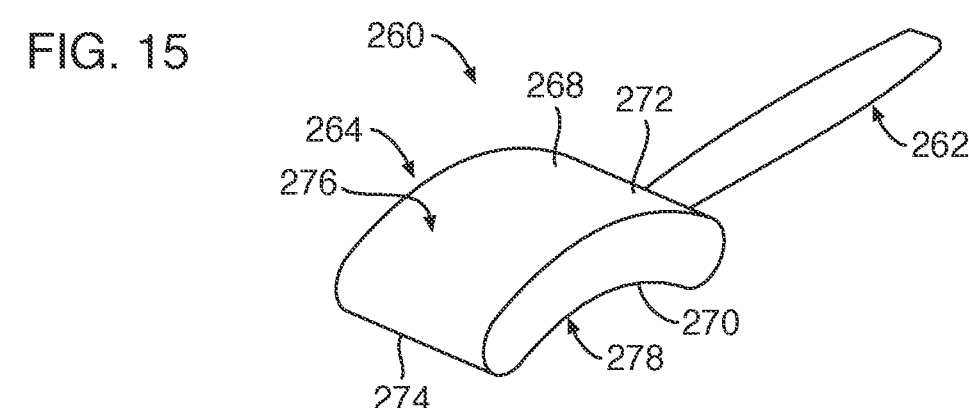
FIG. 16 is a perspective view of another embodiment of a swab device, depicting a swab portion with an elongated structure that extends with a curvature, according to the present invention.

With respect to FIG. 16, another embodiment of a swab device 260 with a handle portion 262 and a swab portion 264 is provided. In this embodiment, the handle portion 262 may be straight. Further, in this embodiment, the swab portion 264 may be elongated with a curve along a length thereof. For example, the swab portion 264 may include a top surface 268 and a bottom surface 270 such that the top surface 268 may define a convex feature 276 from a proximal end 272 to a distal end 274 and the bottom surface 270 may define a concave feature 278 from the proximal end 272 to the distal end 274. The swab portion 264 of this embodiment may be sized and configured to be placed within the patient's cheek to capture saliva produced, for example, from the parotid glands. It should be noted that the swab portion 264 may be positioned to be oriented so that the top surface 268 is positioned against the inner surface of the cheek. In another embodiment, only the top surface 268 or only the bottom surface 270 exhibits either a convex or concave feature.

Figure 17:
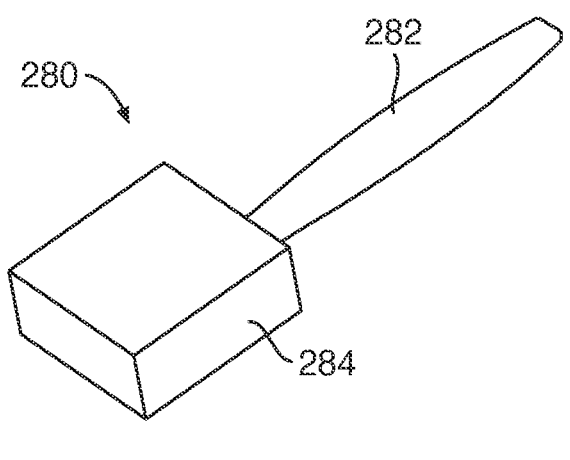
FIG. 17 is a perspective view of another embodiment of a swab device, depicting a swab portion with a block like shape, according to the present invention.
Figure 17A:
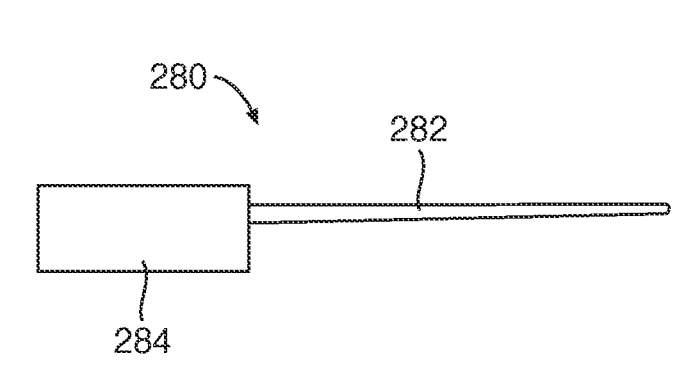
FIG. 17A is a side view of the swab device of FIG. 17, depicting the swab device having a straight handle, according to another embodiment of the present invention.

With respect to FIGS. 17 and 17A, another embodiment of a swab device 280 is provided. The swab device 280 may include a handle portion 282 and a swab portion 284. In this embodiment, the handle portion 282 may be a straight handle, best shown in FIG. 17A. The swab portion 284 may be in block form or the like. The swab portion 284 may be sized and configured to be positioned in the check of the patient for absorbing saliva from the parotid glands, for example. It should be noted that the handle portion 282 of this embodiment may be employed with any of the swab device embodiments described herein.

In another embodiment, any one of the swab devices described herein may include an electrical sensor associated therewith. For example, the electrical sensor may sense when a swab portion has absorbed saliva to a particular capacity, such as 80% or 90%. Otherwise said, the sensor may sense to the user once the swab portion has been saturated to, for example, 80% or 90%. The swab device may also include an indicator element configured to indicate to the user once the swab portion has absorbed saliva to a particular capacity. Such indicator element may be in the form of a light and/or a beeping noise. With this arrangement, the volume of saliva will be known for a given swab portion at the particular capacity, set forth above, as well as the time period taken to absorb the saliva to the particular capacity or saturation level. In this manner, the swab device of this embodiment that includes a sensor may be employed to assess a saliva flow rate.

Figure 18:
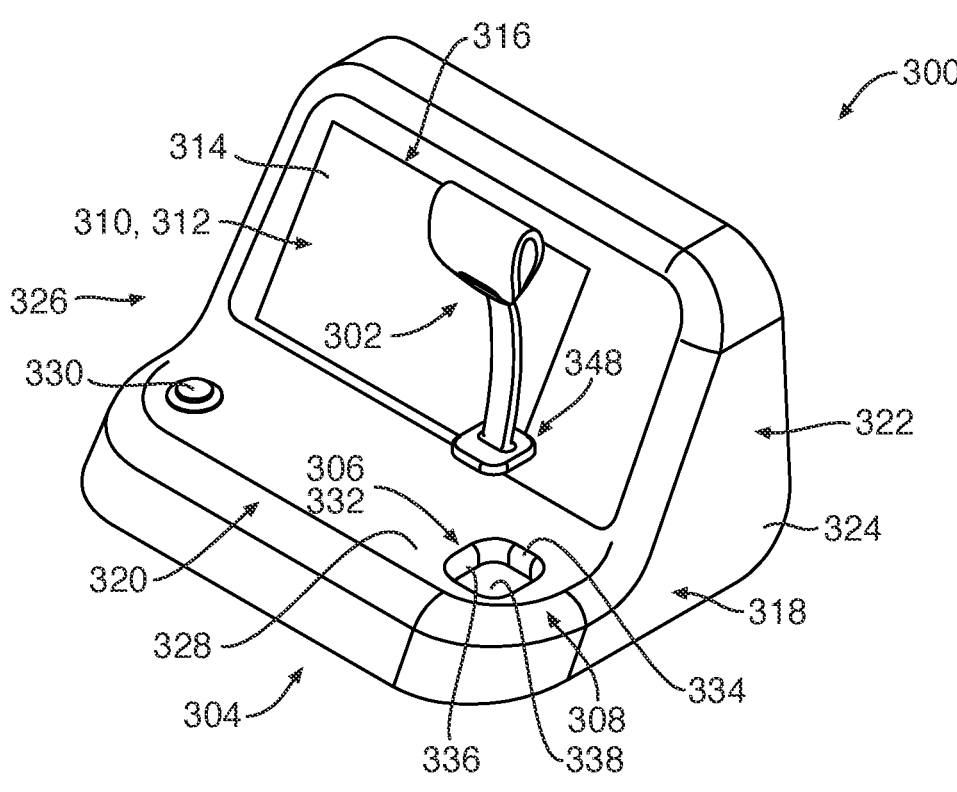
FIG. 18 is a perspective view of another embodiment of a saliva assessment system, depicting a swab device in a dis-engaged position relative to a measuring device, according to the present invention.
Figure 19:
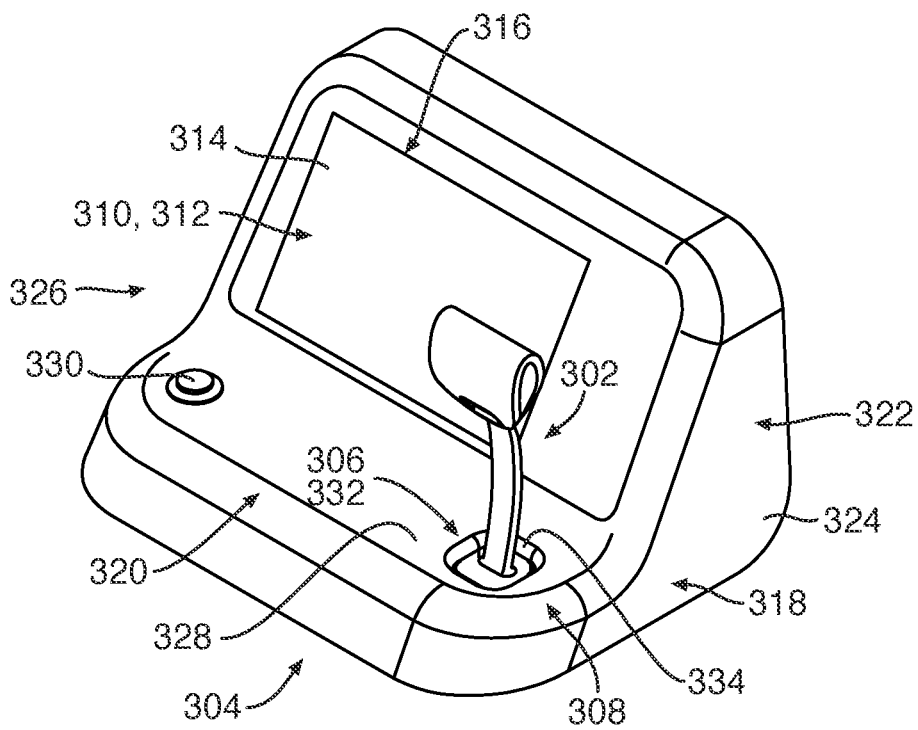
FIG. 19 is a perspective view of the saliva assessment system of FIG. 18, depicting the swab device in an engaged position relative to the measuring device, according to another embodiment of the present invention.

Now with reference to FIGS. 18 and 19, another embodiment of a saliva assessment system 300 is provided. This embodiment may include a swab device 302 and a measuring device 304 that may be employed to function similarly to the saliva assessment system embodiments described and depicted relative to FIGS. 1 and 7. As such, the methods and systems described in previous embodiments for a saliva assessment system may be employed with the saliva assessment system 300 of this embodiment. For example, similar to previous embodiments, the swab device 302 may be moved between a non-engaged position and an engaged position relative to the measuring device 304, the engaged position (see FIG. 19) being a position for weighing saliva collected with the swab device 302 by positioning the swab device 302 within a nesting portion 306 of the measuring device 304. Further, similar to previous embodiments, the measuring device 304 of this embodiment may include a scale portion 308, an input 310 and an output 312. The input 310 may be in the form of key pads and a touch sensitive screen 314 integrated with a display 316. The output 312 may also be in the form of the display 316, for displaying various data, such as a weight of the saliva collected with the swab device 302, patient data, and/or cumulative or comparative patient data. In one embodiment, the measuring device 304 may include a base portion 318 disposed below a platform portion 320 and an upstanding portion 322, the upstanding portion 322 extending upward from a rear portion 324 of the base portion 318. The upstanding portion 322 may include the display 316 along a front side 326 of the upstanding portion 322 and the measuring device 304. The platform portion 320 may include an upper surface 328 that extends flat or horizontally level above the base portion 318 along the front side 326 of the measuring device 304. The platform portion 320 may include a power button 330 or power switch disposed thereon. Such power button 330 or power switch may be at alternative locations on the measuring device 304. Further, the measuring device 304 of this embodiment may be sized and configured to communicate with a remote database 20 and/or a local computing device 126, similar to that described and depicted relative to FIG. 7.

The platform portion 320 may also extend to and define the scale portion 308, the scale portion 308 defining holding structure 332, such as the nesting portion 306, sized and configured to receive the swab device 302 for weighing saliva collected with the swab device 302. For example, the nesting portion 306 may be in the form of a recess 334 defined in the upper surface 328 of the platform portion 320, the recess 334 being sized and configured to receive a proximal most end of the swab device 302 so as to nest together in a nesting arrangement. Further, the recess 334 may be defined with side walls 336 extending downward to a bottom surface 338. The bottom surface 338 of the scale portion 308 being the surface for placing the swab device 302 for measuring purposes, similar to that described in previous embodiments herein.

Figure 20:
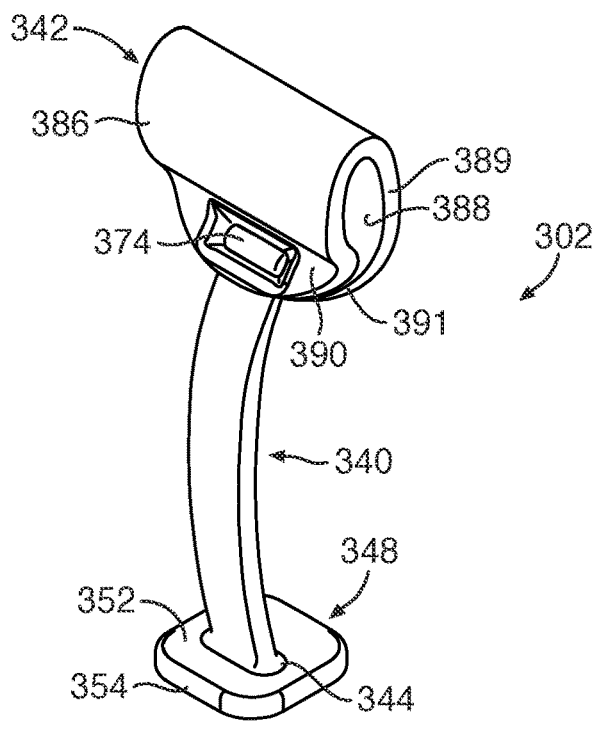
FIG. 20 is a perspective view of the swab device, according to another embodiment of the present invention.
Figure 21:
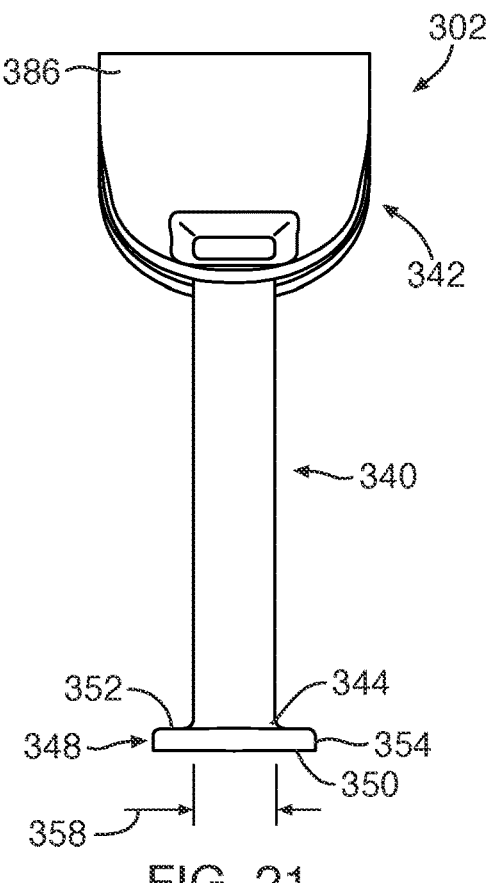
FIG. 21 is a front view of the swab device of FIG. 20, according to the present invention.

Now with reference to FIGS. 20-22, one embodiment of a swab device 302, such as the swab device 302 depicted as being employed with the measuring device of FIGS. 18 and 19, will now be described. As in previous embodiments, the swab device 302 may include a handle portion 340 and a swab portion 342. The handle portion 340 may extend between a first end 344 and a second end 346, the first end 344 being a proximal end and the second end 346 being a distal end. The handle portion 340 may include a base 348 or platform fixedly coupled to the first end 344. Such base 348 may be the proximal most end of the swab device 302. The base 348 may include an underside base surface 350 and an upper base surface 352 with peripheral side walls 354 defined therebetween. The peripheral side walls 354 may extend upward between the underside and upper base surfaces 350, 352 such that the base 348 may exhibit a low profile or somewhat flat profile. The underside and upper base surfaces 350, 352 may extend to exhibit a generally square shape with rounded corners. With this arrangement, such base 348 may be sized and configured to correspond with the peripheral shape defined by the side walls 336 of the recess 334 of the scale portion 308 of the measuring device 304 such that the peripheral side walls 354 extend to be sized slightly smaller than the periphery of the recess 334 (see FIGS. 18 and 19). In this manner, the base 348 of the swab device 302 may be inserted within the recess 334 of the measuring device 304 such that the swab device 302 may sit erect within the recess 334 of the measuring device 304 (see FIG. 19). Further, the underside base surface 350 of the base 348 may be planar so that the swab device 302 may be positioned on any flat surface to sit upright and maintain an upright erect orientation. In another embodiment, the scale portion 308 may define a nesting portion sized and config- ured to receive the handle portion 340 of the swab device 302 so that the handle portion 340 may nest and be posi- tioned in a generally horizontal position or tilted upward from a generally horizontal position.

Figure 23:
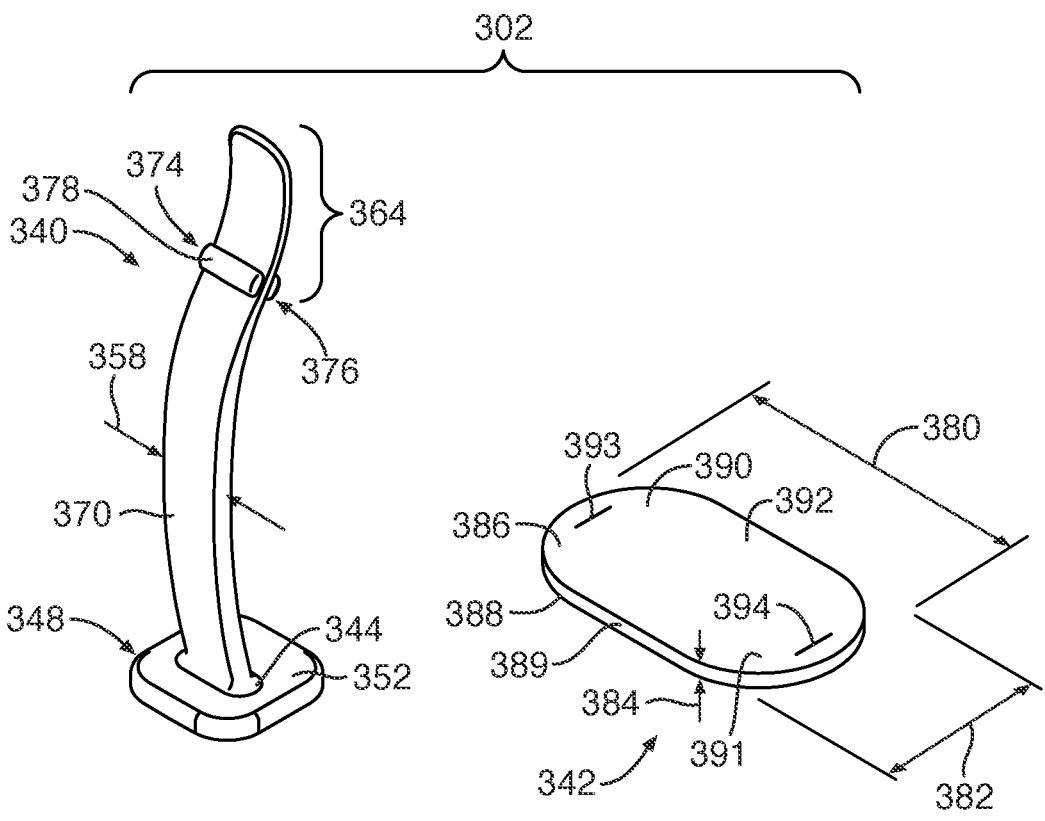
FIG. 23 is an exploded view of the swab device, depicting a swab portion separated from a handle portion of the swab device, according to another embodiment of the present invention.
Figure 24:
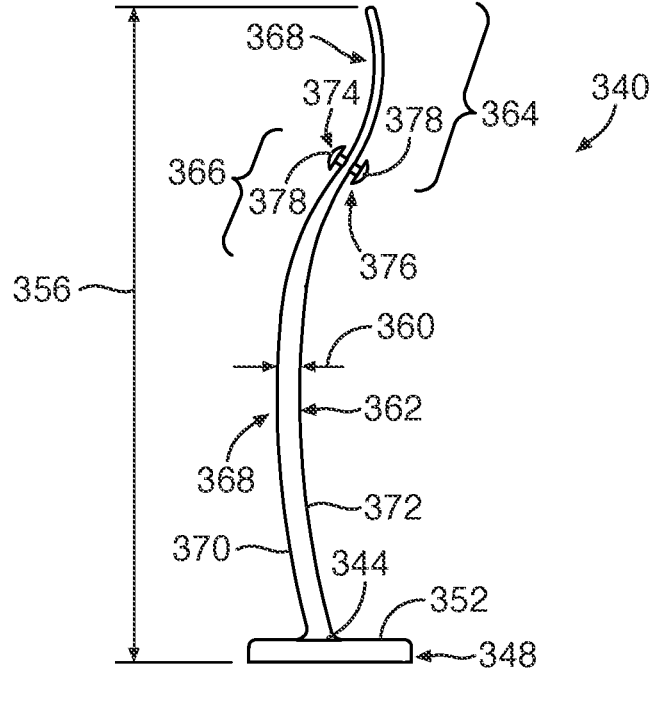
FIG. 24 is a side view of the handle portion of the swab device, according to another embodiment of the present invention.

With reference to FIGS. 23 and 24, description of the handle portion 340 of the swab device 302 will now be described. The first end 344 of the handle portion 340 may extend directly from the upper base surface 352 of the base 348. The handle portion 340 may include a handle 362 and a distal portion 364 extending along a longitudinal length 356, the length 356 extending with a width 358 (see also FIG. 21) and a depth 360 thereof. The dimension of the width 358 may be larger than the dimension of the depth 360, and the dimension of the length 356 may be greater than the dimensions of the width 358 and the depth 360. The depth 360 dimension may taper along a portion of the length 356 of the handle portion 340, such as to define a tapered portion 366. Such tapered portion 366 may extend along a transition between the handle 362 and the distal portion 364 of the handle portion 340. The longitudinal length 356 of the handle portion 340 may extend with one or more curves 368. In one embodiment, the handle portion 340 may extend with two primary curves so as to exhibit an s-type profile (see FIG. 24). Further, the handle portion 340 may define a first surface 370 and a second surface 372 defined along the width 358, the first surface 370 facing opposite relative to the second surface 372 with the depth 360 dimension extending between the first and second surfaces 370, 372. The distal portion 364 of the handle portion 340 may include a first protrusion 374 extending from the first surface 370 and a second protrusion 376 extending from the second surface 372, the first protrusion 374 extending directly opposite the second protrusion 376. Further, the first and second protrusions 374, 376 may be elongated to extend along the width 358 of the handle portion 340. In one embodiment, the first and second protrusions 374, 376 may extend with an enlarged end portion 378. In another embodi- ment, the first and second protrusions 374, 376 with the enlarged end portion 378 may exhibit a mushroom type profile, as depicted in FIG. 24.

Now with reference to FIGS. 20-24, the swab portion 342 will now be described. The swab portion 342 of the swab device 302 may be similar to the swab portion described in previous embodiments herein. For example, the swab por- tion 342 may be sized and configured to be coupled to the distal portion 364 of the handle portion 340 of the swab device 302. The swab portion 342, in a relaxed position, may be a generally flat flexible and resilient structure, as depicted in FIG. 23. In the relaxed position, the swab portion 342 may extend in a generally oval configuration with an elongated length 380, a width 382, and a depth 384 of the swab portion 342. The swab portion 342 may define a first side surface 386 and a second side surface 388 with a periphery 389 therebetween, the periphery 389 defining the depth of the swab portion 342. Further, the swab portion 342 may extend along its length 380 to define opposite first and second end portions 390, 391 with an intermediate portion 392 therebe- tween. The first side surface 386 may define a first slit 393 and a second slit 394 in the respective opposite first and second end portions 390, 391 thereof. The first and second slits 393, 394 may extend through the depth 384 of the swab portion 342 between the first and second side surfaces 386, 388. Further, the first and second slits 393, 394 may be oriented to extend transverse relative to the elongated length 380 of the swab portion 342 and may be sized and config- ured to receive the first and second protrusions 374, 376 of the handle portion 340 to facilitate coupling the swab portion 342 to the handle portion 340. As depicted in FIGS. 20 and 22, the swab portion 342 may be assembled to the handle portion 340 by wrapping or folding the swab portion 342 over the second end 346 or distal end of the handle portion 340 so that the swab portion 342 exhibits a bowed position or bowed configuration around the distal end of the handle portion 340. Such bowed position of the swab portion 342 may be a constrained position of the swab portion 342. Further, in the bowed position, the first and second slits 393, 394 defined in the opposite first and second end portions 390, 391 of the swab portion 342 may facilitate coupling the swab portion 342 to the respective first and second protru- sions 374, 376 of the handle portion 340.

Figure 22:
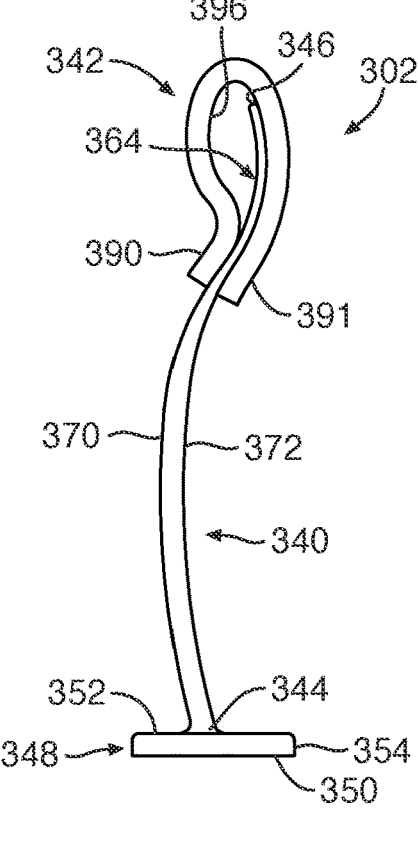
FIG. 22 is a side view of the swab device of FIG. 20, according to the present invention.

As depicted in FIG. 22, the opposite first and second end portions 390, 391 may be held against the opposite first and second surfaces 370, 372 of the handle portion 340 with a portion 396 of the swab portion 342 bowed away or out from one or both of the first and second surfaces 370, 372 adjacent the second end 346 of the handle portion 340. Further, the tapered down and more slender profile of the distal portion 364 of the handle portion 340 may be somewhat flexible. As such, upon a user placing the swab portion 342 in his/her mouth, such as under the tongue, the bowed-out portion 396 of the swab portion 342 and the flexibility of the distal portion 364 of the handle 362 may facilitate the swab portion 342 to comply to the contours under the tongue of the user. In this manner, the swab device 302 may be employed for capturing the saliva within the pours of the swab portion 342 upon the user positioning the swab portion 342 under the tongue.

In another embodiment, a swab device may include a handle portion with an integrated scale for determining a weight of the saliva collected with the swab portion. In still another embodiment, a handle portion of a swab device with, for example, an integrated scale may also include an integrated computing device that may be configured to transmit data to the local computing device 126 and/or the remote database 20 (FIG. 7). In still another embodiment, the swab device 302 may include a strip (not shown) or the like associated with the swab device 302, such as on the swab portion 342, or on the handle portion 340 adjacent the swab portion 342, or a strip included with the system 300 that may measure a pH level of the saliva from the mouth. In another embodiment, the swab portion 342 itself may include an indicator or strip or the like that may indicate a pH level of the saliva from the mouth. In this manner, upon assessing the saliva flow of a person, the pH level of the saliva may also be assessed.

While the invention may be susceptible to various modi- fications and alternative forms, specific embodiments have been shown by way of example in the drawings and have been described in detail herein. Further, the structural features of any one embodiment disclosed herein may be combined or replaced by any one of the structural features of another embodiment set forth herein. As such, it should be understood that the invention is not intended to be limited to the particular forms disclosed. Rather, the invention includes all modifications, equivalents, and alternatives falling within the spirit and scope of the invention as defined by the following appended claims.

What is claimed is:

1. A method for measuring saliva flow in a mouth of a person, comprising:

clearing excess saliva from the mouth;

maintaining the mouth in a closed position for a first predetermined period of time ranging between about 15 seconds and about 5 minutes;

inserting a swab into the mouth for a second predetermined period of time ranging between about 1 second and about 20 seconds; and measuring an amount of saliva captured by the swab by positioning the swab on a measuring device.

2. The method according to claim 1, wherein the clearing comprises:

inserting a pre-test swab into the mouth for a pre-test predetermined period of time ranging between about 1 second and about 20 seconds;

measuring an amount of saliva captured by the pre-test swab by positioning the pre-test swab on the measuring device; and determining whether the measured amount of saliva by the pre-test swab is below a standard healthy saliva amount.

3. The method according to claim 1, wherein the inserting comprises inserting the swab for the second predetermined period of time that ranges between about 1 second and about 10 seconds.

4. The method according to claim 1, wherein the measuring comprises weighing the swab to determine a weight of the saliva.

5. The method according to claim 1, wherein the maintaining comprises maintaining the mouth in the closed position in the range of between about 15 seconds and about three minutes for the first predetermined period of time.

6. The method according to claim 1, wherein the clearing comprises clearing the excess saliva by inserting a secondary swab in the mouth for a period of time ranging between about 1 second and about 5 seconds.

7. The method according to claim 1, wherein the measuring comprises positioning a proximal end of a handle of the swab in an aperture defined in structure of the measuring device.

8. The method according to claim 1, wherein the inserting comprises inserting the swab having a handle portion and a swab portion such that the swab portion comprises an absorbing material configured to absorb saliva collected from the mouth.

9. The method according to claim 1, further comprising transferring patient data including the measured amount to at least one of a local database and a remote data base.

10. The method according to claim 9, wherein the transferring comprises recording information relating to the person and measured data of the person.

11. The method according to claim 9, wherein the transferring comprises transmitting the patient data wirelessly.

12. The method according to claim 9, further comprising processing the patient data to be stored in the at least one of the local database and the remote data base to evaluate the patient data relative to other patient data provided by other patients.

* * * * *